United States Patent
Stroeher et al.

(10) Patent No.: US 10,119,172 B2
(45) Date of Patent: Nov. 6, 2018

(54) METHODS AND REAGENTS FOR DETECTING EBOLA VIRUS

(71) Applicant: The United States of America, as represented by the Secretary, Department of Health and Human Services, Washington, DC (US)

(72) Inventors: Ute Stroeher, Atlanta, GA (US); Tara Sealy, Atlanta, GA (US); Jonathan Towner, Decatur, GA (US); Stuart Nichol, Atlanta, GA (US); César Albariño, Atlanta, GA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/552,157

(22) PCT Filed: Feb. 18, 2016

(86) PCT No.: PCT/US2016/018468
§ 371 (c)(1),
(2) Date: Aug. 18, 2017

(87) PCT Pub. No.: WO2016/134144
PCT Pub. Date: Aug. 25, 2016

(65) Prior Publication Data
US 2018/0044741 A1    Feb. 15, 2018

Related U.S. Application Data

(60) Provisional application No. 62/118,989, filed on Feb. 20, 2015.

(51) Int. Cl.
| | | |
|---|---|---|
| *C12Q 1/68* | (2018.01) | |
| *C12Q 1/70* | (2006.01) | |
| *A61K 39/00* | (2006.01) | |
| *C07H 21/04* | (2006.01) | |
| *A61K 39/12* | (2006.01) | |
| *A61K 38/02* | (2006.01) | |
| *C12Q 1/686* | (2018.01) | |

(52) U.S. Cl.
CPC .............. *C12Q 1/701* (2013.01); *A61K 38/02* (2013.01); *C12Q 1/686* (2013.01)

(58) Field of Classification Search
CPC ...... C12Q 1/6806; C07K 14/005; C12N 7/00; A61K 38/00; A61K 39/12
See application file for complete search history.

(56) References Cited

FOREIGN PATENT DOCUMENTS

| CN | 103045755 | * | 4/2013 |
| WO | WO 2010/048615 | | 4/2010 |

OTHER PUBLICATIONS

Centers for Disease Control and Prevention, "Ebola Virus VP40 Real-Time RT-PCR Assay," dated Nov. 5, 2014, available at http://www.fda.gov/downloads/MedicalDevices/Safety/EmergencySituations/UCM418810.pdf, as retrieved on Apr. 13, 2016.
Centers for Disease Control and Prevention, "Ebola Virus NP Real-Time RT-PCR Assay," dated Nov. 5, 2014, available at http://www.fda.gov/downloads/MedicalDevices/Safety/EmergencySituations/UCM418815.pdf, as retrieved on Apr. 13, 2016.
Southern, et al. "Comparison of FilmArray and quantitative real-time reverse transcriptase PCR for detection of Zaire ebolavirus from contrived and clinical specimens." *Journal of Clinical Microbiology* 53, No. 9 (2015): 2956-2960.

* cited by examiner

*Primary Examiner* — Barry A Chestnut
(74) *Attorney, Agent, or Firm* — Klarquist Sparkman, LLP

(57) ABSTRACT

Probes and primers are disclosed for detecting EBOV nucleic acid in a sample. Methods are also disclosed that utilize these probes and primers, wherein the methods can be used to detect an EBOV in a sample to identify a subject with an EBOV infection.

24 Claims, 5 Drawing Sheets
Specification includes a Sequence Listing.

PCR Amplification vs Cycle: example.opd

PCR Amplification vs Cycle: example.opd

PCR Amplification vs Cycle: example4.opd

PCR Amplification vs Cycle: example4.opd

PCR Amplification vs Cycle: example3.opd

PCR Amplification vs Cycle: example3.opd

METHODS AND REAGENTS FOR DETECTING EBOLA VIRUS

CROSS REFERENCE TO RELATED APPLICATIONS

This is the U.S. National Stage of International Application No. PCT/US2016/018468, filed Feb. 18, 2016, which was published in English under PCT Article 21(2), which in turn claims the benefit of U.S. Provisional Application No. 62/118,989, filed Feb. 20, 2015. The provisional application is incorporated by reference herein in its entirety.

FIELD

This application relates to the field of viral infection, particularly to methods and compositions for identifying Ebola virus in a sample.

BACKGROUND

Ebola virus disease (EVD) is a viral disease in humans and non-human primates caused by virus within the genus *Ebolavirus*. These viruses are single-stranded negative sense RNA viruses in the family Filoviridae. Within the genus *Ebolavirus*, five species of have been identified, 4 of which are found in Africa (*Zaire ebolavirus, Sudan ebolavirus, Cote d'Ivoire ebolavirus*, and *Bundibugyo ebolavirus*). *Zaire ebolavirus*, also referred to as Ebola virus or EBOV, is the most common cause of EVD, and has led to the most deaths attributed to EVD. The clinical presentation of EVD is characterized by an acute febrile illness with fever, headache, myalgias, abdominal pain, nausea, vomiting, and diarrhea. Hemorrhagic symptoms, high case fatality, and person-to-person transmission are common in EVD outbreaks.

Keys to controlling EVD outbreaks include active case identification and isolation of patients from the community to prevent continued virus spread. Diagnosis of acute cases of EBOV infection is made most commonly through detection of viral RNA in blood, typically using a PCR-based detection assay. However, current PCR-based methodologies for detecting EBOV infection are limited due to nucleic acid variability across different viral strains within the EBOV species. Accordingly, there is a need for a rapid and robust assay for cross-strain detection of EBOV viruses.

SUMMARY

Probes and primers are disclosed herein for detecting EBOV nucleic acid. The primers and probes can be used, for example, for detection of EBOV nucleic acid molecules of the NP or VP40 genes. Although the *Zaire ebolavirus* species has significant cross-strain nucleic acid variation, the disclosed primers and probes can be used to detect at least 95% of known EBOV strains. The probes and primers can be labeled. Kits are provided that include these probes and primers.

Methods are disclosed herein for detecting EBOV NP nucleic acid in a biological sample. In some embodiments, the method can comprise amplifying a DNA template produced from a reverse transcription reaction performed on nucleic acid containing RNA isolated from the biological sample. Amplifying the DNA template comprises contacting the DNA template under conditions suitable for amplification with a set of forward and reverse primers that can be used to amplify an EBOV nucleic acid molecule comprising the sequence set forth as SEQ ID NO: 1, and performing a polymerase chain reaction amplification (such as a real-time polymerase chain reaction) to form an amplified DNA product. The method further comprises contacting the amplified DNA product with a probe that can hybridize to the amplified DNA product, wherein hybridization of the probe to the amplified DNA product indicates that EBOV NP nucleic acid is present in the sample. In some embodiments, the set of forward and reverse primers can comprise a forward primer and a reverse primer comprising, consisting essentially of, or consisting of the nucleic acid sequences set forth as SEQ ID NO: 2 (NP2-F) and SEQ ID NO: 3 (NP2-R), respectively. In some embodiments, the set of forward and reverse primers can comprise a forward primer comprising, consisting essentially of, or consisting of the nucleic acid sequence set forth as SEQ ID NO: 2 (NP2-F), and a pair of reverse primers comprising, consisting essentially of, or consisting of the nucleic acid sequences set forth as SEQ ID NOs: 15 (NP2-R1) and 16 (NP2-R2). In some embodiments, the probe can comprise, consist essentially of, or consist of the nucleotide sequence set forth as SEQ ID NO: 4 (NP2-P), or the complement thereof.

Methods are disclosed herein for detecting EBOV VP40 nucleic acid in a biological sample. In some embodiments, the method can comprise amplifying a DNA template produced from a reverse transcription reaction performed on nucleic acid containing RNA isolated from the biological sample. Amplifying the DNA template comprises contacting the DNA template under conditions suitable for amplification with a set of forward and reverse primers that can be used to amplify an EBOV nucleic acid molecule comprising the sequence set forth as SEQ ID NO: 5, and performing a polymerase chain reaction amplification (such as a real-time polymerase chain reaction) to form an amplified DNA product. The method further comprises contacting the amplified DNA product with a probe that can hybridize to the amplified DNA product, wherein hybridization of the probe to the amplified DNA product indicates that EBOV NP nucleic acid is present in the sample. In some embodiments, the forward primer and the reverse primer can comprise, consist essentially of, or consist of the nucleic acid sequences set forth as SEQ ID NO: 6 (VP40-F) and SEQ ID NO: 7 (VP40-R), respectively. In some embodiments, the set of forward and reverse primers can comprise a pair of forward primers comprising, consisting essentially of, or consisting of the nucleic acid sequences set forth as SEQ ID NOs: 9 (VP40-F1) and 10 (VP40-F2), and a pair of reverse primers comprising, consisting essentially of, or consisting of the nucleic acid sequences set forth as SEQ ID NOs: 11 (VP40-R1) and 12 (VP40-R2). In some embodiments, the probe can comprise, consist essentially of, or consist of the nucleotide sequence set forth as SEQ ID NO: 8 (VP40-P) or the complement thereof. In some embodiments, the probe can comprise a pair of oligonucleotides comprising, consisting essentially of, or consisting of the nucleic acid sequences set forth as SEQ ID NOs: 13 (VP40-P1) and 14 (VP40-P2), or the complements thereof.

In several embodiments, the methods of detecting an EBOV nucleic acid molecule in a biological sample from a subject can further include identification of the subject having an EBOV infection. Such subjects can be selected for treatment and/or treated with a therapeutically effective amount of an anti-Ebola therapy.

The foregoing and other features and advantages of this disclosure will become more apparent from the following detailed description of several embodiments which proceeds with reference to the accompanying figures.

SEQUENCE LISTING

Figure 1:
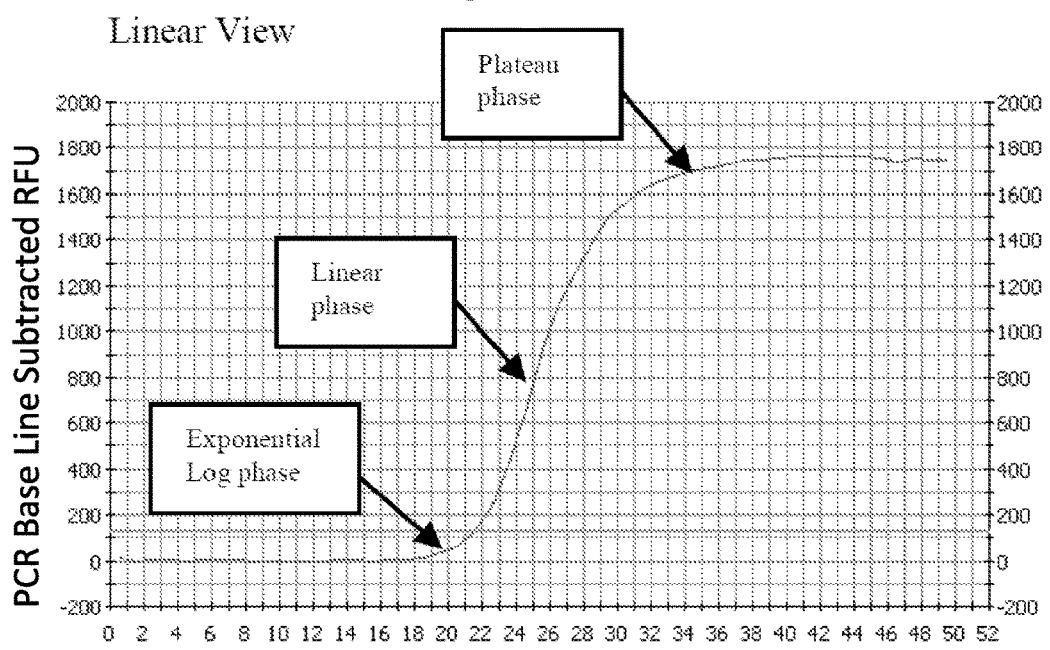
FIG. 1 is a set of graphs showing the linear and log views of an RT-PCR amplification curve of EBOV nucleic acid using the VP40 primer and probe set, noting each stage of the amplification curve.
Figure 1:
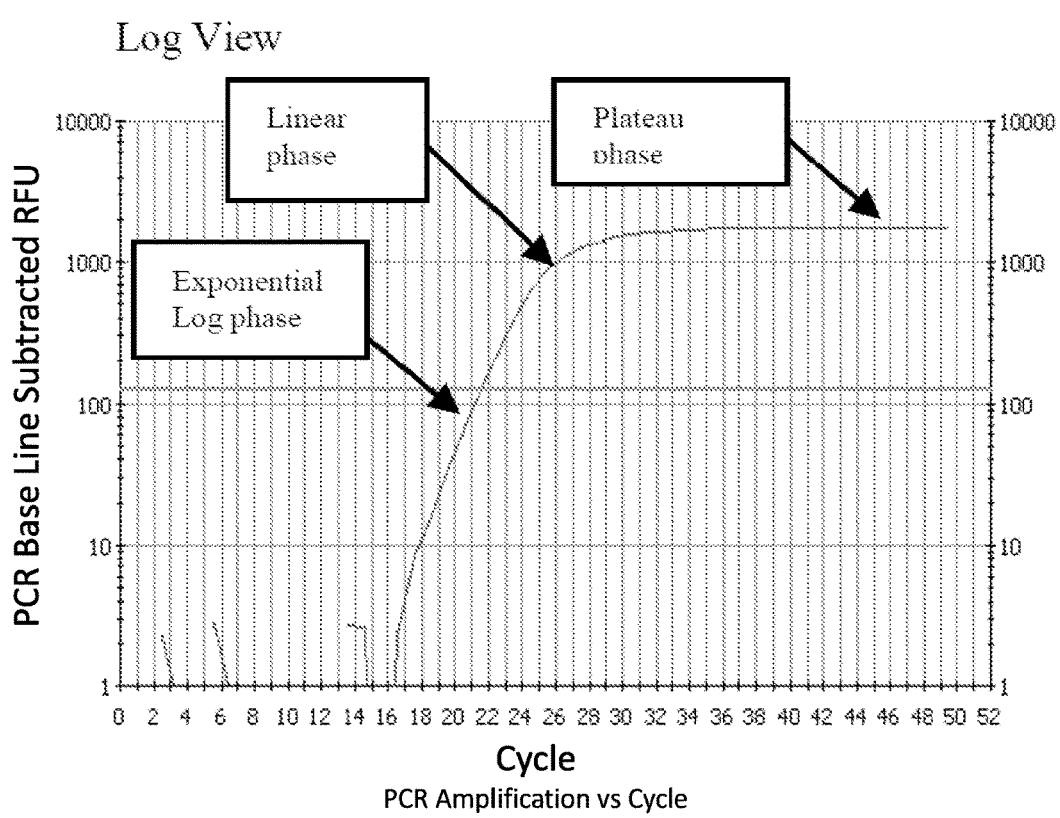

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~4 kb), which was created on Aug. 3, 2017, which is incorporated by reference herein. In the accompanying sequence listing:

SEQ ID NO: 1 is a nucleic acid sequence of an EBOV NP gene.

ATTGCTGCCAGCAGTATCTAGTGGGAGAAACATTAAGAGAACACTTGCTG

CCATGCCGGAAGAGGAGACGACTGAAGCTAATGCCGGTCAGTTCCTCTCC

TTTGCAAGTCTATTCCTTC

SEQ ID NO: 2 is an oligonucleotide primer for amplification of a nucleotide sequence of EBOV NP gene (NP2-F).

AATTGCTGCCAGCAGTATCTAGTGG

SEQ ID NO: 3 is an oligonucleotide primer for amplification of a nucleotide sequence of EBOV NP gene (NP2-R).

GAAGGAATAGACTTGCAAARGAGAG, wherein R is A or G

SEQ ID NO: 4 is an oligonucleotide probe for detection of a nucleotide sequence of EBOV NP gene (NP2-P).

TCTCCTCTTCCGGCATGGCAGCAAGTGTTCTC

SEQ ID NO: 5 is a nucleic acid sentience of a fragment of the EBOV VP40 gene

TGCGTCCAGGAATTTCATTTCATCCAAAACTTCGCCCCATTCTTTTACCC

AACAAAAGTGGGAAGAA

SEQ ID NO: 6 is an oligonucleotide primer for amplification of a nucleotide sequence of EBOV VP40 gene (VP40-F).

TGCGYCCAGGAATTTCA, wherein Y = C or T

SEQ ID NO: 7 is an oligonucleotide primer for amplification of a nucleotide sequence of EBOV VP40 gene (VP40-R).

TTCTTCCCACTYTTGTTGGGTAA, wherein Y = C or T

SEQ ID NO: 8 is an oligonucleotide probe for detection of a nucleotide sequence of EBOV VP40 gene (VP40-P).

TCATCCAAAACTKCGCCCCATTCT, wherein K = G or T

SEQ ID NO: 9 is an oligonucleotide primer for amplification of a nucleotide sequence of EBOV VP40 gene (VP40-F1).

TGCGCCCAGGAATTTCA

SEQ ID NO: 10 is an oligonucleotide primer for amplification of a nucleotide sequence of EBOV VP40 gene (VP40-F2).

TGCGTCCAGGAATTTCA

SEQ ID NO: 11 is an oligonucleotide primer for amplification of a nucleotide sequence of EBOV VP40 gene (VP40-R1).

TTCTTCCCACTCTTGTTGGGTAA

SEQ ID NO: 12 is an oligonucleotide primer for amplification of a nucleotide sequence of EBOV VP40 gene (VP40-R2).

TTCTTCCCACTTTTGTTGGGTAA

SEQ ID NO: 13 is an oligonucleotide probe for detection of a nucleotide sequence of EBOV VP40 gene (VP40-P1).

TCATCCAAAACTGCGCCCCATTCT

SEQ ID NO: 14 is an oligonucleotide probe for detection of a nucleotide sequence of EBOV VP40 gene (VP40-P2).

TCATCCAAAACTTCGCCCCATTCT

SEQ ID NO: 15 is an oligonucleotide probe for detection of a nucleotide sequence of EBOV NP gene (NP2-R1).

GAAGGAATAGACTTGCAAAAGAGAG

SEQ ID NO: 16 is an oligonucleotide probe for detection of a nucleotide sequence of EBOV NP gene (NP2-R2).

GAAGGAATAGACTTGCAAAGGAGAG

DETAILED DESCRIPTION

I. Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008. As used herein, the term "comprises" means "includes." As used herein, the singular forms "a," "an," and "the," refer to both the singular as well as plural, unless the context clearly indicates otherwise. As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

3' end: The end of a nucleic acid molecule that does not have a nucleotide bound to it 3' of the terminal residue.

5' end: The end of a nucleic acid sequence where the 5' position of the terminal residue is not bound by a nucleotide.

Administration: To provide or give a subject an agent by any effective route. Exemplary routes of administration for agents include, but are not limited to, oral, injection (such as subcutaneous, intramuscular, intradermal, intraperitoneal, and intravenous), sublingual, transdermal (e.g., topical), intranasal and inhalation routes.

Agent: Any substance or any combination of substances that is useful for achieving an end or result; for example, a substance or combination of substances useful for inhibiting EBOV infection in a subject. Agents include proteins, antibodies, nucleic acid molecules, compounds, small molecules, organic compounds, inorganic compounds, or other molecules of interest. An agent can include a therapeutic agent, a diagnostic agent or a pharmaceutical agent. Agents include effector molecules and detectable markers. In some embodiments, the agent is a polypeptide agent (such as an EBOV-neutralizing antibody), or an anti-viral agent. The skilled artisan will understand that particular agents may be useful to achieve more than one result.

Amplification: A technique that increases the number of copies of a nucleic acid molecule (such as an RNA or DNA). An example of amplification is polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques.

Other examples of amplification include real-time polymerase chain reaction (RT-PCR), strand displacement amplification, as disclosed in U.S. Pat. No. 5,744,311; transcription-free isothermal amplification, as disclosed in U.S. Pat. No. 6,033,881; repair chain reaction amplification, as disclosed in PCT publication WO 90/01069; ligase chain reaction amplification, as disclosed in European patent publication EP-A-320,308; gap filling ligase chain reaction amplification, as disclosed in U.S. Pat. No. 5,427,930; and NASBA RNA transcription-free amplification, as disclosed in U.S. Pat. No. 6,025,134. Several embodiments include multiplex qPCR assays, which are useful for amplifying and detecting multiple nucleic acid sequences (such as nucleic acid of NP and VP40 EBOV genes) in a single reaction.

Biological sample: A sample of biological material obtained from a subject. Biological samples include all clinical samples useful for detection of disease or infection (e.g., EBOV virus infection) in subjects. Appropriate samples include any conventional biological samples, including clinical samples obtained from a human or veterinary subject. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, cerebrospinal fluid (CSF), etc.), tissue biopsies or autopsies, fine-needle aspirates, and/or tissue sections. In a particular example, a biological sample is obtained from a subject having, suspected of having or at risk of having, EBOV infection.

Complementary. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions. In particular examples disclosed herein, the complementary sequence is complementary at a labeled nucleotide, and at each nucleotide immediately flanking the labeled nucleotide.

Consists of or consists essentially of: With regard to a polynucleotide (such as a probe or primer), a polynucleotide consists essentially of a specified nucleotide sequence if it does not include any additional nucleotides. However, the polynucleotide can include additional non-nucleic acid components, such as labels (for example, fluorescent, radioactive, or solid particle labels), sugars or lipids. With regard to a polynucleotide, a polynucleotide that consists of a specified nucleotide sequence does not include any additional nucleotides, nor does it include additional non-nucleic acid components, such as lipids, sugars or labels.

Contacting: Placement in direct physical association, for example solid, liquid or gaseous forms. Contacting includes, for example, direct physical association of fully- and partially-solvated molecules.

Control: A sample or standard used for comparison with an experimental sample. In some embodiments, the control is a sample obtained from a healthy patient, such as a tissue sample obtained from a patient that is not infected with EBOV. In other embodiments, the control can be from a patient that is infected with EBOV. In some embodiments, the control is a sample including EBOV nucleic acid. In still other embodiments, the control is a historical control or standard reference value or range of values (such as a previously tested control sample, such as a group of EBOV patients with known prognosis or outcome, or group of samples that represent baseline or normal values, such as the presence or absence of ZOBOV nucleic acid in a biological sample.

Detecting: To identify the existence, presence, or fact of something. General methods of detecting are known to the skilled artisan and may be supplemented with the protocols and reagents disclosed herein. For example, included herein are methods of detecting an EBOV nucleic acid in a biological sample. In some examples, detecting an EBOV nucleic acid in a biological sample detects EBOV infection in the subject from whom the biological sample was obtained. Detection can include a physical readout, such as fluorescence or a reaction output.

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Ebola Virus (EBOV): Also known as *Zaire ebolavirus*, EBOV is an enveloped, non-segmented, negative-sense, single-stranded RNA virus that causes Ebola virus disease (EVD), formerly known as Ebola hemorrhagic fever (EHF), in humans. EVOV spreads through human-to-human transmission, with infection resulting from direct contact with blood, secretions, organs or other bodily fluids of infected people, and indirect contact with environments contaminated by such fluids (see, e.g., Baize et al., *N Engl J Med.*, 371, 1418-1425, 2014, which is incorporated by reference herein).

In humans, EBOV has an initial incubation period of 2 to 21 days (7 days on average, depending on the strain) followed by a rapid onset of non-specific symptoms such as fever, extreme fatigue, gastrointestinal complaints, abdominal pain, anorexia, headache, myalgias and/or arthralgias. These initial symptoms last for about 2 to 7 days after which more severe symptoms related to hemorrhagic fever occur, including hemorrhagic rash, epistaxis, mucosal bleeding, hematuria, hemoptysis, hematemesis, melena, conjunctival hemorrhage, tachypnea, confusion, somnolence, and hearing loss. In general, the symptoms last for about 7 to 14 days after which recovery may occur. Death can occur 6 to 16 days after the onset of symptoms (Geisbert and Jahrling, *Nat Med.*, 10, S110-21. 2004; Hensley et al., *Curr Mol Med*, 5, 761-72, 2005). People are infectious as long as their blood and secretions contain the virus; the virus was isolated from semen 61 days after onset of illness in a man who was infected in a laboratory (Baize et al., *N Engl J Med.*, 371, 1418-1425, 2014).

The EBOV genome includes about 19K nucleotides, which encode seven structural proteins and one non-structural protein, including NP (a nucleoprotein), VP35 (a polymerase cofactor), VP40 (a matrix protein), VP30 (a transcription activator), VP24, L (a RNA polymerase), and GP (a glycoprotein).

Hybridization: The terms "annealing" and "hybridization" refer to the formation of base pairs between complementary regions of DNA, RNA, or between DNA and RNA of nucleic acids. Examples of annealing and hybridization include formation of base pairs between two separate nucleic acid molecules, as well as formation of base pairs between nucleic acids on a single nucleic acid molecule.

In some examples, hybridization is between two complementary nucleic acid sequences, for example nucleic acid sequences that are at least 90% complementary to each other, such as at least 91%, 92%, 93%, 94%, 95%, 96%, 97%, 98%, 99%, or 100% complementary to each other.

In additional embodiments, hybridization conditions resulting in particular degrees of stringency and specificity will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 50% Identity)
Hybridization: 6×SSC at RT to 55° C. for 16-20 hours
Wash at least twice: 2×-3×SSC at RT to 55° C. for 20-30 minutes each.

In some embodiments, the probes and primers disclosed herein can hybridize to nucleic acid molecules under low stringency, high stringency, and very high stringency conditions.

Inhibiting or treating a disease or condition: Inhibiting the full development of a disease or condition, for example, in a subject who is at risk of or has an EBOV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in viral titer, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid molecule or protein) has been substantially separated or purified away from other biological components in the cell of the organism in which the component naturally occurs. The term "isolated" does not require absolute purity. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

Label: A detectable molecule (also known as a label) that is conjugated directly or indirectly to a second molecule, such as a nucleic acid molecule, to facilitate detection of the second molecule. The person of ordinary skill in the art is familiar with detectable markers for labeling nucleic acid molecules and their use. For example, the detectable marker can be capable of detection by ELISA, spectrophotometry, flow cytometry, or microscopy. Specific, non-limiting examples of detectable markers include fluorophores, fluorescent proteins, chemiluminescent agents, enzymatic linkages, radioactive isotopes and heavy metals or compounds. In several embodiments, the detectable markers are designed for use with PCR, such as RT-PCR. Various methods of labeling nucleic acid molecules are known in the art and may be used. A "unique" label is a label that is distinct from others in a reaction, such that the identity of a single bound molecule can be known when the label is detected.

Multiplex RT-PCR: Amplification and detection of multiple nucleic acid species in a single RT-PCR reaction. By multiplexing, target nucleic acids can be amplified in single tube. In some examples, multiplex PCR permits the simultaneous detection of the amplification products of two regions of the EBOV genome using the disclosed primers and probes.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In some examples, a nucleic acid encodes a disclosed antigen.

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide. Nucleotides include those nucleotides containing modified bases, modified sugar moieties and modified phosphate backbones, as known in the art.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences." Unless denoted otherwise, whenever a polynucleotide sequence is represented, it will be understood that the nucleotides are in 5' to 3' orientation from left to right.

Probes and primers: Probe are nucleic acid molecules (e.g., a DNA oligonucleotide, usually of 100 or fewer nucleotide residues) attached to a detectable label or reporter molecule, which is used to detect a complementary target nucleic acid molecule by hybridization and detection of the label or reporter. Isolated oligonucleotide probes (which as defined herein also include the complementary sequence and corresponding RNA sequences) are of use for detection of EBOV nucleic acid sequences. Typically, probes are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 nucleotides in length. For example, a probe can be about 10-100 nucleotides in length, such as, 12-15, 12-20, 12-25, 12-30, 12-35, 12-40, 12-45, 12-50, 12-80, 14-15, 14-16, 14-18, 14-20, 14-25, 14-30, 15-16, 15-18, 15-20, 15-25, 15-30, 15-35, 15-40, 15-45, 15-50, 15-80, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 20-80, 21-22, 21-25, 21-30, 22-25, 22-30, 22-40, 22-50, 23-24, 23-25, 23-30, 24-25, 24-30, 25-35, 25-30, 25-35, 25-40, 25-45, 25-50 or 25-80 nucleotides in length. In some embodiments, the probe can be labeled with a datable moiety that provides a detectable signal (such as an optically detectable signal). In some embodiments, the label can be a synthetic label. In some embodiments, the probe can be labeled with a terminally-linked fluorophore and a terminally-linked non-fluorescent quencher for use in a RT-PCR assay.

Primers are nucleic acid molecules, usually DNA oligonucleotides of about 10-50 nucleotides in length (longer lengths are also possible). Typically, primers are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 nucleotides in length. For example, a primer can be about 10-50 nucleotides in length, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40 or 25-45, 25-50 nucleotides in length.

Probes and primers can also be of a maximum length, for example no more than 15, 25, 25, 40, 50, 75 or 100 nucleotides in length.

Primers may be annealed to a complementary target DNA strand by nucleic acid hybridization to form a hybrid between the primer and the target DNA strand, and then extended along the target DNA strand by a DNA polymerase enzyme. One of skill in the art will appreciate that the hybridization specificity of a particular probe or primer typically increases with its length. Thus, for example, a probe or primer including 20 consecutive nucleotides typically will anneal to a target with a higher specificity than a corresponding probe or primer of only 15 nucleotides. In some embodiments, probes and primers are used in combination in a RT-PCR reaction.

Operably linked: A first molecule, such as a nucleic acid or protein, is operably linked with a second molecule when the first molecule is placed in a functional relationship with the second molecule. For instance, a promoter is operably linked to a nucleic acid coding sequence if the promoter affects the transcription or expression of the coding sequence. Additionally, an intron is operably linked to an exon for the function of splicing. Generally, operably linked nucleotide sequences are contiguous.

Primer pair: Two primers (one "forward" and one "reverse") that can be used for amplification of a nucleic acid sequence, for example by polymerase chain reaction (PCR) or other in vitro nucleic-acid amplification methods. The forward and reverse primers of a primer pair do not hybridize to overlapping complementary sequences on the target nucleic acid sequence.

Real-Time PCR (RT-PCR): A method for detecting and measuring products generated during each cycle of a PCR, which are proportionate to the amount of template nucleic acid prior to the start of PCR. The information obtained, such as an amplification curve, can be used to determine the presence of a target nucleic acid (such as an EBOV nucleic acid) and/or quantitate the initial amounts of a target nucleic acid sequence. Exemplary procedures for RT-PCR can be found in "Quantitation of DNA/RNA Using Real-Time PCR Detection" published by Perkin Elmer Applied Biosystems (1999); *A-Z of Quantitative PCR*, Bustin (ed.), International University Line, La Jolla, Calif., 2004; and *Quantitative Real-Time PCR in Applied Microbiology*, Filion (Ed), Caister Academic Press, 2012.

In some examples, the amount of amplified target nucleic acid (for example an EBOV nucleic acid) can be detected using a labeled probe, such as a probe labeled with a fluorophore, for example a TAQMAN® probe. In other examples, the amount of amplified target nucleic acid can be detected using a DNA intercalating dye. The increase in fluorescence emission is measured in real-time, during the course of the RT-PCR assay. This increase in fluorescence emission is directly related to the increase in target nucleic acid amplification. In some examples, the change in fluorescence (Delta Rn; dRn; ΔRn) is calculated using the equation $dRn=Rn^+ - Rn^-$, with $Rn^+$ being the fluorescence emission of the product at each time point and Rn being the fluorescence emission of the baseline. The dRn values are plotted against cycle number, resulting in amplification plots for each sample.

The threshold cycle (Ct) is the PCR cycle number at which the fluorescence emission (dRn) exceeds a chosen threshold, which is typically 10 times the standard deviation of the baseline (this threshold level can, however, be changed if desired). The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(-1/slope)}$, for example. The efficiency of the PCR should be 90-100% meaning doubling of the amplicon at each cycle. This corresponds to a slope of −3.1 to −3.6 in the $C_t$ vs. log-template amount standard curve.

Sensitivity and specificity: Statistical measurements of the performance of a binary classification test. Sensitivity measures the proportion of actual positives which are correctly identified (e.g., the percentage of samples that are identified as including nucleic acid from a particular virus). Specificity measures the proportion of negatives which are correctly identified (e.g., the percentage of samples that are identified as not including nucleic acid from a particular virus).

Sequence identity: The similarity between two nucleic acid sequences, is expressed in terms of the similarity between the sequences, otherwise referred to as sequence identity. Sequence identity is frequently measured in terms of percentage identity, similarity, or homology; a higher percentage identity indicates a higher degree of sequence similarity.

The NCBI Basic Local Alignment Search Tool (BLAST), Altschul et al., *J. Mol. Biol.* 215:403-10, 1990, is available from several sources, including the National Center for Biotechnology Information (NCBI, Bethesda, Md.), for use in connection with the sequence analysis programs blastp, blastn, blastx, tblastn and tblastx. It can be accessed through the NCBI website. A description of how to determine sequence identity using this program is also available on the website.

When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described on the NCBI website.

These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al.; and Tijssen, *Hybridization With Nucleic Acid Probes, Part I: Theory and Nucleic Acid Preparation*, Laboratory Techniques in Biochemistry and Molecular Biology, Elsevier Science Ltd., 1993.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Specifically binds: A nucleic acid sequence that, under a defined set of reaction conditions, binds to its complement and not to other nucleic acid sequences. A probe that specifically binds to its target can be used in RT-PCR assays.

Subject: Any mammal, such as humans, non-human primates, pigs, sheep, cows, rodents and the like. In two non-limiting examples, a subject is a human subject or a murine subject. Thus, the term "subject" includes both human and veterinary subjects.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of which is intended. In some examples, a target nucleic acid includes a region of EBOV virus genome. Purification or isolation of the target nucleic acid molecule, if needed, can be conducted by methods known to those in the art, such as by using a commercially available purification kit or the like.

Therapeutically effective amount: The amount of an agent (such as an anti-EBOV agent) or therapy, that alone, or together with one or more additional agents, induces the desired response, such as, for example treatment of EBOV infection in a subject. Ideally, a therapeutically effective amount provides a therapeutic effect without causing a substantial cytotoxic effect in the subject. In some examples, an anti-EBD therapy can include oral rehydration therapy and/or administration of intravenous fluids.

A therapeutically effective amount of an agent or therapy that is administered to a human or veterinary subject will vary depending upon a number of factors associated with that subject, for example the overall health of the subject. A therapeutically effective amount can be determined by varying the dosage and measuring the resulting therapeutic response, such as the reduction of symptoms associated with EBOV infection. The agents can be administered in a single dose, or in several doses, as needed to obtain the desired response. However, the therapeutically effective amount of can be dependent on the source applied, the subject being treated, the severity and type of the condition being treated, and the manner of administration.

Under conditions sufficient for: A phrase that is used to describe any environment that permits a desired activity. In one example the desired activity is amplification of a nucleic acid molecule.

II. Description of Several Embodiments

Methods for Detecting EBOV Nucleic Acid in a Sample

Methods are disclosed for amplifying and detecting nucleic acid targets in a sample, wherein the targets are EBOV nucleic acid sequences, for example the nucleotide sequences of an EBOV VP40 and/or NP gene. Thus, in some embodiments, the methods include detecting the presence (or absence) of EBOV nucleic acid in a biological sample from a subject. Detection of EBOV nucleic acid in the biological sample from a subject can be used to identify the subject as having an EBOV infection.

One advantage of the disclosed EBOV nucleic acid detection assays is that the disclosed methods can detect EBOV nucleic acid from at least 95% (such as at least 98%, at least 99%, or all) known EBOV strains. Thus, using the disclosed methods, it is possible to detect EBOV nucleic acid in a sample in a single assay, without the need for multiple assays.

The biological sample used in a disclosed assay can be selected from any clinical samples useful for detection of disease or infection (e.g., EBOV infection) in a subject. Exemplary biological samples include, without limitation, cells, cell lysates, blood smears, cytocentrifuge preparations, cytology smears, bodily fluids (e.g., blood, plasma, serum, saliva, sputum, urine, bronchoalveolar lavage, semen, CSF, etc.), tissue biopsies or autopsies, fine-needle aspirates, and/or tissue sections. In one embodiment, the biological sample is a urine sample. In another embodiment, the biological sample is a serum sample. In a particular example, a biological sample is obtained from a subject having, suspected of having or at risk of having, an EBOV infection. Standard techniques for acquisition of such samples can be used. The sample can be used directly or can be processed, such as by adding solvents, preservatives, buffers, or other compounds or substances. In some embodiments, nucleic acids are isolated from the sample. DNA or RNA can be extracted using standard methods. For instance, rapid RNA preparation can be performed using a commercially available kit (e.g., the Qiagen QIAamp DSP Viral RNA Mini kitQiagen, Inc., Valencia, Calif.; or the Dynal BeadRetriever® System). The RNA preparation technique can be chosen to yield a nucleotide preparation that is accessible to and amenable to nucleic acid amplification.

EBOV is a negative sense RNA virus. Therefore, in several embodiments, a reverse transcription assay is performed on nucleic acid material extracted from the biological sample to generate DNA complementary to EBOV RNA. The complementary DNA can include the NP and/or VP40 DNA used as temple in the subsequent RT-PCR assay. The person of ordinary skill in the art is familiar with methods of performing a reverse transcription assay on a sample containing nucleic acid material. In several embodiments the reverse transcription assay can be performed on a sample prior to set up of the RT-PCR assay (for example in embodiments using a two-step rRT-PCR assay). In other embodiments the reverse transcription assay can be performed in the same reaction assay as the RT-PCR assay (for example in embodiments using a one-step rRT-PCR assay). In some embodiments, the SuperScript® III Platinum® One-Step qRT-PCR Kit (available from Invitrogen Corp, Cat. No. 11732-088) can be used in one-step rRT-PCR assays.

Several embodiments of the method disclosed herein include use of PCR, such as RT-PCR. PCR reaction conditions typically include either two or three step cycles. Two step cycles have a denaturation step followed by a hybridization/elongation step. Three step cycles include a denaturation step followed by a hybridization step during which the primer hybridizes to the strands of DNA, followed by a separate elongation step. The polymerase reactions are incubated under conditions in which the primers hybridize to the target sequences and are extended by a polymerase. The amplification reaction cycle conditions are selected so that the primers hybridize specifically to the target sequence and are extended.

Several embodiments include RT-PCR, which is used to simultaneously quantify and amplify a specific part of a given nucleic acid molecule. It can be used, for example, to determine whether or not a specific sequence is present in the sample. In quantitative applications, RT-PCR can be used to determine the copy number of a nucleic acid molecule in a sample.

RT-PCR monitors the fluorescence emitted during the reaction as an indicator of amplicon production during each PCR cycle, as opposed to endpoint detection. The real-time progress of the reaction can be viewed in some systems. Typically, RT-PCR uses the detection of a fluorescent reporter. The fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed. Thus, the procedure follows the general pattern of polymerase chain reaction, but the nucleic acid molecule is quantified after each round of amplification. In several embodiments, the amplified nucleic acid molecule can be detected by the use of fluorescent dye that intercalates with double-strand DNA. In other embodiments, an amplified nucleic acid molecule can be detected by use of oligonucleotide probes labeled with a reporter fluorophore that can be detected in the RT-PCR assay.

Primers for use in a disclosed PCR assay are typically designed so that all of the primers participating in a particular reaction have melting temperatures that are within at least five degrees Celsius, and more typically within two degrees Celsius of each other. Primers are further designed to avoid priming on themselves or each other. Primer concentration should be sufficient to bind to the amount of target sequences that are amplified so as to provide an accurate assessment of the quantity of amplified sequence. Those of skill in the art will recognize that the amount of concentration of primer will vary according to the binding affinity of the primers as well as the quantity of sequence to be bound. Typical primer concentrations will range from 0.01 µM to 0.5 µM.

In a typical three-step PCR cycle, a sample including a DNA polynucleotide and a PCR reaction cocktail can be denatured by treatment in a thermal cycler at about 90-98° C. for 10-90 seconds. The denatured polynucleotide is then hybridized to oligonucleotide primers by treatment in a thermal cycler at a temperature of about 30-65° C. for 0.5-2 minutes. Chain extension then occurs by the action of a DNA polymerase on the polynucleotide annealed to the oligonucleotide primer. This reaction typically occurs at a temperature of about 50-72° C. for 30 seconds to 5 minutes.

In an exemplary two-step PCR cycle, the sample including the DNA polynucleotide and the PCR reaction cocktail can be denatured by treatment in a thermal cycler at about 90-98° C. for 10-90 seconds. The hybridization and extension phases are combined in a single step of treatment in a thermal cycler at a temperature of about 30-65° C. for 1-5 minutes. Any desired number of PCR cycles may be carried out depending on variables including but not limited to the amount of the initial DNA polynucleotide, the length of the desired product and primer stringency. The above temperature ranges and the other numbers are exemplary and not intended to be limiting. These ranges are dependent on other factors such as the type of enzyme, the type of container or plate, the type of biological sample, the size of samples, etc. One of ordinary skill in the art will recognize that the temperatures, time durations and cycle number can readily be modified as necessary. Exemplary reaction conditions are disclosed in the examples section below.

In some embodiments, the method includes combining a sample comprising EBOV NP and/or VP40 nucleic acid targets and forward and reverse primer pairs for priming amplification of the nucleic acid targets. In further embodiments, one or more probes complementary to EBOV NP and/or VP40 nucleic acid target sequences can also be included in the reaction. The probes can be uniquely labeled. A RT-PCR assay can be performed and any amplified product detected (for example using a labeled probe) to determine if EBOV NP or VP40 nucleic acid molecule is present in the sample.

In certain embodiments, the methods are used for the detection of an EBOV NP nucleic acid, such as a nucleic acid having the sequence set forth as SEQ ID NO: 1. The method can include the use of primers that are, for example, 17 to 30 nucleotides in length, such as 20 to 30 nucleotides, such as 24 to 28 nucleotides in length. In some examples, the forward and/or reverse primers can be 18, 19, 20, 21, 22, 23, 24, 25, 26, 27, 28, 29, or 30 nucleotides in length. In some embodiments, the forward and reverse primers used the RT-PCR assay can comprise, consist essentially of, or consist of the nucleic acid sequences set forth as SEQ ID NO: 2 and SEQ ID NO: 3, respectfully, or the complements thereof. An oligonucleotide probe can be included in the assay for detection of amplified product, for example a probe comprising, consisting essentially of, or consisting of the nucleic acid sequence set forth as SEQ ID NO: 4, or the complement thereof. In some embodiments, the RT-PCR assay can be performed using a forward primer comprising, consisting essentially of, or consisting of the nucleic acid sequence set forth as SEQ ID NO: 2, and can further include a pair of reverse primers comprising, consisting essentially of, or consisting of the nucleic acid sequences set forth as SEQ ID NOs: 15 and 16, respectfully. In some embodiments, the RT-PCR assay can be performed using a forward primer comprising, consisting essentially of, or consisting of the complement of the nucleic acid sequence set forth as SEQ ID NO: 2, and can further include a pair of reverse primers comprising, consisting essentially of, or consisting of the complements of the nucleic acid sequences set forth as SEQ ID NOs: 15 and 16, respectfully. In several embodiments, the SEQ ID NOs: 15 and 16 primers can be included in the reaction at a ratio (e.g., molar ratio) of about 50/50. As used herein in the context of ratios of oligonucleotides, "about" refers to ±5%. The primers can be included in the reaction at a ratio (e.g., molar ratio) of about 50/(25/25) forward/(2 reverse) primers (that is, the primers in the primer set include about 50% SEQ ID NO: 2, about 25% SEQ ID NO: 15, and about 25% SEQ ID NO: 16, by molar ratio). The composition can optionally include a probe comprising, consisting essentially of, or consisting of the nucleic acid sequence set forth as SEQ ID NO: 4, or the complement thereof. The probe can optionally be labelled with a detectable marker for use in RT-PCR assays (such as TAQMAN® assays). For example the probe can be labeled with a terminally-linked FAM fluorophore and a terminally-linked BHQ quencher.

In certain embodiments, the methods are used for the detection of an EBOV VP40 nucleic acid, such as a nucleic acid having the sequence set forth as SEQ ID NO: 5. The method can include the use of primers that are, for example, 17 to 30 nucleotides in length, such as 20 to 30 nucleotides, such as 24 to 28 nucleotides in length. In some examples, the forward and/or reverse primers can be 18, 19, 20, 21, 22, 23, 24, 25, 26, 27, 28, 29, or 30 nucleotides in length. In some embodiments, the forward and reverse primers used the RT-PCR assay can comprise, consist essentially of, or consist of the nucleic acid sequences set forth as SEQ ID NO: 6 and SEQ ID NO: 7, respectfully, or the complements thereof. An oligonucleotide probe can be included in the assay for detection of amplified product, for example a probe comprising, consisting essentially of, or consisting of the nucleic acid sequence set forth as SEQ ID NO: 8, or the complement thereof. In some embodiments, the RT-PCR assay can be performed using a pair of forward primers comprising, consisting essentially of, or consisting of the nucleic acid sequences set forth as SEQ ID NO: 9 and 10, respectfully, and a pair of reverse primers comprising, consisting essentially of, or consisting of the nucleic acid sequences set forth as SEQ ID NOs: 11 and 12, respectfully. In some embodiments, the RT-PCR assay can be performed using a pair of forward primers comprising, consisting essentially of, or consisting of the complements of the nucleic acid sequences set forth as SEQ ID NO: 9 and 10, respectfully, and a pair of reverse primers comprising, consisting essentially of, or consisting of the complements of the nucleic acid sequences set forth as SEQ ID NOs: 11 and 12, respectfully. The primers can be included at a ratio (e.g., molar ratio) of about (25/25)/(25/25) of (2 forward)/(2 reverse) primers (that is, the primers in the primer set include about 25% SEQ ID NO: 9, about 25% SEQ ID NO: 10, about 25% SEQ ID NO: 11, and about 25% SEQ ID NO: 12, by molar ratio. The composition can optionally include a pair of probes comprising, consisting essentially of, or consisting of the complements of the nucleic acid sequences set forth as SEQ ID NO: 13 and 14, respectfully. The probes can be included at a ratio (e.g., molar ratio) of about 50/50. The probes can optionally be labelled with a detectable mark for use in RT-PCR assays (such as TAQMAN® assays). For example the probe can be labeled with a terminally-linked FAM fluorophore and a terminally-linked BHQ quencher.

The skilled artisan will appreciate that detecting the presence or absence (or amount or proportion) of the target nucleic acid molecule as described herein using RT-PCR assays can include detecting the target nucleic acid molecule after a particular amplification cycle of the RT-PCR assay. For example, after 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50 amplification cycles of the RT-PCR assay, or at least that may cycles, or no more than that many cycles.

In some embodiments, the oligonucleotide probe used in a disclosed assay can be labeled, for example with a base-linked or terminally-linked fluorophore and non-fluorescent quencher for use in RT-PCR assays. Fluorophores for use in RT-PCR assays are known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). Fluorophores can be conjugated to the oligonucleotides, for example by post-synthesis modification of oligonucleotides that are synthesized with reactive groups linked to bases. Useful fluorophores include: fluorescein, fluorescein isothiocyanate (FITC), carboxy tetrachloro fluorescein (TET), NHS-fluorescein, 5 and/or 6-carboxy fluorescein (FAM), 5-(or 6-) iodoacetamidofluorescein, 5-{[2(and 3)-5-(Acetylmercapto)-succinyl]amino} fluorescein (SAMSA-fluorescein), 5'-hexachloro-fluorescein (HEX), 6-carboxy-4',5'-dichloro-2',7'dimethoxyfluorescein, succinimidyl ester (JOE) and other fluorescein derivatives, rhodamine, Lissamine rhodamine B sulfonyl chloride, Texas red sulfonyl chloride, 5 and/or 6 carboxy rhodamine (ROX) and other rhodamine derivatives, coumarin, 7-amino-methyl-coumarin, 7-Amino-4-methylcoumarin-3-acetic acid (AMCA), and other coumarin derivatives, BODIPY fluorophores, Cascade Blue fluorophores such as 8-methoxypyrene-1,3,6-trisulfonic acid trisodium salt, Lucifer yellow fluorophores such as 3,6-Disulfonate-4-amino-naphthalimide, phycobiliproteins derivatives, Alexa fluor dyes (available from Molecular Probes, Eugene, Oreg.) and other fluorophores known to those of skill in the art. For a general listing of useful fluorophores, see also Hermanson, G. T., BIOCONJUGATE TECHNIQUES (Academic Press, San Diego, 1996).

Quenchers for use in RT-PCR assays are also known in the art and include, for example, 6-carboxytetramethylrhodamine, succinidyl ester (6-TAMRA; TAMRA) and non-fluorescent quencher (NFP) such as the BHQ-0, BHQ-1, BHQ-2, and BHQ-3 quenchers available from Biosearch Technologies. The person of ordinary skill in the art is familiar with quenchers for use with TAQMAN™ probes, and such reagents are available from several commercial sources.

In certain embodiments, the amplified products are directly visualized with detectable label such as a fluorescent DNA-binding dye. In one embodiment the amplified products are quantified using an intercalating dye, including but not limited to SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin. For example, a DNA binding dye such as SYBR green binds double stranded DNA and an increase in fluorescence intensity can be measured. For example, the fluorescent dsDNA dye can be added to the buffer used for a PCR reaction. The PCR assay can be performed in a thermal cycler, and after each cycle, the levels of fluorescence are measured with a detector, such as a camera. The dye fluoresces much more strongly when bound to dsDNA (e.g., amplified PCR product). Because the amount of the dye intercalated into the double-stranded DNA molecules is typically proportional to the amount of the amplified DNA products, the amount of amplified nucleic acid can be quantified by detecting the fluorescence of the intercalated dye using detection instruments known in the art. When referenced to a standard dilution, the dsDNA concentration in the PCR can be determined.

In addition to various kinds of fluorescent DNA-binding dye, other luminescent labels such as sequence specific oligonucleotide probes can be employed in the amplification reaction to facilitate the detection and quantification of the amplified product. Probe based quantitative and/or real-time amplification relies on the sequence-specific detection of a desired amplified product. Unlike the dye-based quantitative methods, it utilizes target-specific probe labeled with a detectable marker such as a base-linked or terminally-linked fluorophore and quencher. Such markers are known to the person of ordinary skill in the art and described herein. Further, methods for performing probe-based quantitative amplification are well established in the art.

For detection using oligonucleotide probes, the reaction is prepared as usual for PCR conditions, with the addition of the sequence specific labeled oligonucleotide probe. After denaturation of the DNA, the labeled probe is able to bind to its complementary sequence in the region of interest of the template DNA. When the PCR reaction is heated to the proper extension temperature, the polymerase is activated and DNA extension proceeds. As the polymerization continues it reaches the labeled probe bound to the complementary sequence of DNA. The polymerase breaks the probe into separate nucleotides, and separates the fluorescent reporter from the quencher. This results in an increase in fluorescence as detected by the optical assembly. As PCR cycle number increases more and more of the fluorescent reporter is liberated from its quencher, resulting in a well-defined geometric increase in fluorescence. This allows accurate determination of the final, and initial, quantities of DNA.

In one embodiment, the fluorescently-labeled probes (such as probes disclosed herein) rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a donor fluorophore and an acceptor or quencher fluorophore on the same probe (for example, using a molecular beacon or a TAQMAN™ probe) can identify a probe that specifically hybridizes to the DNA sequence of interest. In some embodiments, the fluorescently-labeled DNA probes used to identify amplification products have spectrally distinct emission wavelengths, thus allowing them to be distinguished within the same reaction tube, for example in multiplex PCR, such as a multiplex RT-PCR.

Any type of thermal cycler apparatus can be used for the amplification of, for example, EBOV nucleic acids, as described above and/or the determination of hybridization. Examples of suitable apparatuses include PTC-100® Peltier Thermal Cycler (MJ Research, Inc.; San Francisco, Calif.), a ROBOCYCLER® 40 Temperature Cycler (Agilent/Stratagene; Santa Clara, Calif.), or GeneAmp® PCR System 9700 (Applied Biosystems; Foster City, Calif.). For RT-PCR, any type of real-time thermocycler apparatus can be used. For example, ICYCLER IQ™ or CFX96™ real-time detection systems (Bio-Rad, Hercules, Calif.), LIGHTCYCLER® systems (Roche, Mannheim, Germany), a 7700 Sequence Detector (Perkin Elmer/Applied Biosystems; Foster City, Calif.), ABI™ systems such as the 7000, 7300, 7500, 7700, 7900, or ViiA7 systems (Applied Biosystems; Foster City, Calif.), or an MX4000™, MX3000™ or MX3005™ qPCR system (Agilent/Stratagene; Santa Clara, Calif.), DNA ENGINE OPTICON® Continuous Fluorescence Detection System (Bio-Rad, Hercules, Calif.), ROTOR-GENE® Q real-time cycler (Qiagen, Valencia, Calif.), or SMARTCYCLER® system (Cepheid, Sunnyvale, Calif.) can be used to amplify and detect nucleic acid sequences in real-time. In some embodiments, RT-PCR is performed using a TAQMAN® array format, for example, a microfluidic card in which each well is pre-loaded with primers and probes for a particular target. The reaction is initiated by adding a sample including nucleic acids and assay reagents (such as a PCR master mix) and running the reactions in a real-time thermocycler apparatus.

The disclosed EBOV detection assays can detect EBOV nucleic acid from at least 90% (such as at least 91%, at least 92%, at least 93%, at least 94%, at least 95%, at least 96%, at least 97%, at least 98%, at least 99%, or even 100%) of EBOV isolates. In some embodiments, the disclosed methods can predict with a sensitivity of at least 90% and/or a specificity of at least 90% for the identity of an EBOV nucleic acid molecule in a biological sample, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%.

In several embodiments, detection of EBOV nucleic acid in the biological sample from a subject can be used to identify the subject as having an EBOV infection. For example, the method can include detecting an EBOV nucleic acid molecule in a biological sample from a subject using any of the RT-PCR assays described herein, such as an RT-PCR assay using the primers and probes for detecting EBOV NP or VP40 nucleic acid as described herein.

In one non-limiting embodiment, a first assay using the NP2 primers and probes as described herein for detection of EBOV NP nucleic acid in a biological sample is performed to identify a subject as having an EBOV infection, and the results of the first assay are confirmed by performing a second RT-PCR assay using the VP40 primers and probes for detection of EBOV VP40 nucleic acid in a biological sample as described herein. In another non-limiting embodiment, a first assay using the VP40 primers and probes for detection of EBOV VP40 nucleic acid in a biological sample as described herein is performed to identify a subject as having an EBOV infection, and the results of the first assay are confirmed by performing a second RT-PCR assay using the NP2 primers and probes for detection of EBOV NP nucleic acid in a biological sample as described herein.

If a subject is identified as having an EBOV infection, the disclosed methods can also include EBOV infection in the subject. For example, the method can include administering a therapeutically effective amount of an anti-ebola agent or anti-ebola therapy to a subject identified as having an EBOV infection. In a non-limiting example, the subject with EBOV infection can be administered a therapeutically effective amount of an anti-viral agent, and/or oral rehydration therapy and/or administration of intravenous fluids.

III. Isolated Nucleic Acid Molecules and Compositions Comprising Same

Isolated oligonucleotide primers (which as defined herein also include the complementary sequence and corresponding RNA sequences) for use in the disclosed methods, and compositions comprising such primers, are provided herein.

The isolated oligonucleotide primers can comprise or consist of at least 10 consecutive nucleotides (such as at least 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides) from a target nucleic acid sequence (e.g., an EBOV sequence). For example, in some embodiments, the isolated oligonucleotide primers can include or consist of 10-50 nucleotides, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40, 25-45, or 25-50 consecutive nucleotides from a target nucleic acid sequence.

In some embodiments, any of the probes or primers disclosed herein can be of a maximum length, for example no more than 15, 20, 25, 30, 35, 40, 50, 75, 100, or 150 nucleotides in length. Any of the isolated nucleic acid sequences disclosed herein may consist or consist essentially of the disclosed sequences, or include nucleic acid molecules that have a maximum length of 15, 20, 25, 30, 35, 40, 45, 50, 55, 60, 65, 70, 75 or 80 contiguous nucleotides of the disclosed sequence. The disclosed contiguous sequences may also be joined at either end to other unrelated sequences.

In some embodiments, the oligonucleotide primers or probes can comprise, consist essentially of, or consist of the sequence of any one of the primers listed herein, such as any one of SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16. These oligonucleotides can be employed as effective oligonucleotide primers or probes for amplification and/or detection of target nucleic acid molecule sequences.

Compositions comprising one or more of the probes or primers disclosed herein are also provided, and are useful, for example, in the disclosed methods. In some such embodiments, the composition is useful in methods for detecting an EBOV nucleic acid molecule, such as an EBOV VP40 or NP nucleic acid molecule.

In some embodiments, the composition for amplification of a NP nucleic acid can include a forward primer and a reverse primer, comprising, consisting essentially of, or consisting of the nucleic acid sequences set forth as SEQ ID NOs: 2 and 3, respectfully. The composition can optionally include a probe comprising, consisting essentially of, or consisting of the nucleic acid sequence set forth as SEQ ID NO: 4.

In some embodiments, the composition can include a forward primer comprising, consisting essentially of, or consisting of the nucleic acid sequence set forth as SEQ ID NO: 2, and can further include a pair of reverse primers comprising, consisting essentially of, or consisting of the nucleic acid sequences set forth as SEQ ID NOs: 15 and 16, respectfully. The primers can be included at a ratio of about 50/(25/25) forward/(2 reverse) primers in the composition. The composition can optionally include a probe comprising, consisting essentially of, or consisting of the nucleic acid sequence set forth as SEQ ID NO: 4.

In some embodiments, the composition for amplification of a VP40 nucleic acid can include a forward primer and a reverse primer, comprising, consisting essentially of, or consisting of the nucleic acid sequences set forth as SEQ ID NOs: 6 and 7, respectfully. The composition can optionally include a probe comprising, consisting essentially of, or consisting of the nucleic acid sequence set forth as SEQ ID NO: 8.

In some embodiments, the composition can include a pair of forward primers comprising, consisting essentially of, or consisting of the nucleic acid sequences set forth as SEQ ID NO: 9 and 10, respectfully, and can further include a pair of reverse primers comprising, consisting essentially of, or consisting of the nucleic acid sequences set forth as SEQ ID NOs: 11 and 12, respectfully. The primers can be included at a ratio of about (25/25)/(25/25) of (2 forward)/(2 reverse) primers. The composition can optionally include a pair of probes comprising, consisting essentially of, or consisting of the nucleic acid sequences set forth as SEQ ID NO: 13 and 14, respectfully. The probes can be included at a ratio of about 50/50.

The isolated nucleic acid molecules and/or compositions disclosed herein can be supplied in the form of a kit for use in an assay to identify or characterize a target nucleic acid molecule. In such a kit, an appropriate amount of one or more of the primers disclosed herein, are provided in one or more containers. A nucleic acid probe may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. Control reagents, such as control nucleic acid molecules can also be included.

In some examples, one or more sets of primers, may be provided in pre-measured single use amounts in individual, typically disposable, tubes or equivalent containers. With such an arrangement, the sample to be tested for the presence of the target nucleic acids can be added to the individual tube(s) and amplification carried out directly.

The amount of nucleic acid probe supplied in the kit can be any appropriate amount, and may depend on the target market to which the product is directed. For instance, if the kit is adapted for research or clinical use, the amount of each nucleic acid primer provided would likely be an amount sufficient to prime several detection reactions.

In some embodiments, kits also may include the reagents necessary to carry out RT-PCR assays, including sample preparation reagents, appropriate buffers, salts, tubes or assay cells. In other particular embodiments, the kit includes equipment, reagents, and instructions for extracting and/or purifying nucleic acid molecules from a sample.

EXAMPLES

The following examples are provided to illustrate particular features of certain embodiments, but the scope of the claims should not be limited to those features exemplified Example 1

Detection of EBOV Nucleic Acid

This example illustrates one-step reverse-transcriptase/real-time PCR (rRT-PCR) assay for the amplification of EBOV nucleic acid from biological samples.

Methods
Nucleic Acid Extraction

Nucleic acid was extracted from whole blood, serum, plasma, and urine using the Dynal BeadRetriever™ System (Life Technologies, catalog #159-50) according to the manufacturer's protocol. Sample extractions should yield RNA or total nucleic acid of sufficient volume to cover all the rRT-PCR assays planned for a particular assay (a minimum of 60 µL is recommended). Alternative extraction systems can also be used, such as the MagMAX™ Express-96 Deep Well Magnetic Particle Processor or the QIAGEN QIAamp DSP Viral RNA Mini Kit. A human specimen control (CDC; catalog # HS0096 (500 µL/vial) was included in each extraction run as a sample extraction control. Specimen extracts were frozen or retained in cold block or on ice until performing the RT-PCR assay.

Primers and Probes
NP2 Primers and Probe Set:

```
Forward primer, NP2-F:
                                       (SEQ ID NO: 2)
AATTGCTGCCAGCAGTATCTAGTGG.

Reverse Primer, NP2-R:
                                       (SEQ ID NO: 3)
GAAGGAATAGACTTGCAAARGAGAG, wherein R is A or G.
```

In the assays described herein, reference to NP2-R primer refers to a 50/50 mix of two primers: GAAGGAATAGACTTGCAAAAGAGAG (SEQ ID NO: 15, NP2-R1) and GAAGGAATAGACTTGCAAAGGAGAG (SEQ ID NO: 16. NP2-R2). Thus, reference to "NP2 primers and probes" refers to three primers and one probe, as discussed above.

```
Probe, NP2-P:
                                       (SEQ ID NO: 4)
TCTCCTCTTCCGGCATGGCAGCAAGTGTTCTC.
```

A real-time PCR assay performed with the NP2 primers and probes list above is referred to an EBOV NP2 rRT-PCR Assay.

VP40 Primers and Probe Set:

Forward primer, VP40-F: TGCGYCCAGGAATTTCA, wherein Y is C or T (SEQ ID NO: 6).

In the assays described herein, reference to VP40-F primer refers to a 50/50 mix of two primers: TGCGCCCAGGAATTTCA (SEQ ID NO: 9, VP40-F1) and TGCGTCCAGGAATTTCA (SEQ ID NO: 10, VP40-F2).

Reverse primer, VP40-R: TTCTTCCCACTYTTGTTGGGTAA, wherein Y is C or T (SEQ ID NO: 7). Reference to VP40-R primer refers to a 50/50 mix of two primers:

```
                                       (SEQ ID NO: 11, VP40-R1)
TTCTTCCCACTCTTGTTGGGTAA
and
                                       (SEQ ID NO: 12, VP40-R2)
TTCTTCCCACTTTTGTTGGGTAA.
```

Probe, VP40-P: TCATCCAAAACTKCGCCCCATTCT, wherein K is G or T (SEQ ID NO: 8). Reference to VP40-P probe refers to a 50/50 mix of two primers:

```
                                       (SEQ ID NO: 13, VP40-P1)
TCATCCAAAACTGCGCCCCATTCT
and
                                       (SEQ ID NO: 14, VP40-P1)
TCATCCAAAACTTCGCCCCATTCT.
```

A real timer PCR assay performed with the VP40 primers and probes list above is referred to as an EBOV VP40 rRT-PCR Assay.

Thus, reference to "VP40 primers and probes" refers to four primer and two probes, as discussed above. RP primers and probe set: Forward primer, RP-F; Reverse primer, RP-R, Probe, RP-P.

These probes and primers were only handled in a clean area and stored at appropriate temperatures in the dark. Freeze-thaw cycles were avoided. Lyophilized reagents were resuspended in 0.25 mL PCR grade nuclease-free water (50× working concentration) and allowed to rehydrate for 15 minutes at room temperature in the dark before further dilution. The probes were conjugated to the FAM and BHQ fluorophore and quencher for TAQMAN® RT-PCR assays.

rRT-PCR

The Invitrogen SuperScript® III Platinum® One-Step qRT-PCR Kit was used for the one-step rRT-PCR assays. Buffer, enzyme, primer/probes, and reaction mix solutions were mixed by inversion 5 times, briefly centrifuged, and returned to ice. Each rRT-PCR reaction included:

| | |
|---|---|
| 2X Reaction Mix = | 12.50 µl |
| SuperScript ® III RT/Platinum Taq Mix = | 0.50 µl |
| Forward primer (50 µM stock) = | 0.50 µl |
| Reverse primer (50 µM stock) = | 0.50 µl |
| Probe (5 µM) = | 0.50 µl |
| ROX = | 0.05 µl |
| Water, nuclease-free = | 5.45 µl |
| Total volume = | 20.00 µl |
| Sample RNA (or control sample) = | 5 µl |

EBOV nucleic acids were amplified using a one-step reverse-transcriptase real-time PCR (rRT-PCR) assay using the AB 7500 Fast Dx RT-PCR machine. The cycle times utilized were as follows:

| Step | Cycles | Temp | Time |
|---|---|---|---|
| Reverse transcription | 1 | 50° C. | 15 min |
| Taq inhibitor inactivation | 1 | 95° C. | 2 min |
| PCR Amplification | 40 | 95° C. | 15 sec |
| | | 55° C. | 60 sec |

The instrument settings were set as follows: Detector: FAM, Quencher: None, Passive Reference: ROX, Run Mode: Standard, Sample Volume: 25 µL.

Controls

Control reactions included a no-template control of nuclease free water (NTC), a human specimen control without EBOV nucleic acid (HSC), and a positive control containing EBOV NP nucleic acid or EBOV VP40 nucleic acid.

The HSC included a human biological sample that does not include any EBOV nucleic acid, and was extracted and processed with each batch of specimens to be tested. The final volume of eluted RNA from the HSC was approximately equal to the volume of extracted control material. For example, 100 µl of starting HSC control material resulted in about 100 µl of RNA extract. The RNA extracted from the HSC was not diluted before testing. 5 µl of extracted RNA was used in each extraction control assay. The expected Ct value for RNase P amplification from HSC rRT-PCR control is <35. No amplification should be observed from this control using the NP or VP40 primers and probes.

EBOV NP rRT-PCR Positive Control (EBOV-NP-PC) and EBOV VP40 rRT-PCR Positive Control (EBOV-VP40-PC) included NP or VP40 RNA from EBOV. 5 µl of positive control was added to each positive control rRT-PCR reaction. The expected Ct value for the HSC rRT-PCR control is <35 using the NP or VP40 primers and probes.

Evaluation of Results

Accurate interpretation of rRT-PCR results requires careful consideration of several assay parameters. Generally:

If the RT-PCR assay yields a positive amplification curve within 38 cycles, the specimen is considered positive for EBOV.

If the RT-PCR assay yields a positive amplification curve at or above 38 cycles, the specimen is considered equivocal for EBOV.

If the RT-PCR assay does not yield a positive amplification curve using EVOB specific primers and probe, and the control RT-PCR assay (e.g., using RNase P (RP) primers and probe) yields a positive amplification curve (CT<40), the specimen is considered negative for EBOV.

If the RT-PCR assay does not yield a positive amplification curve using EVOB specific primers and probe, and the control RT-PCR assay (e.g., using RP primers and probe) also does not yield a positive amplification curve (CT<40), then the specimen is considered inconclusive for EBOV.

For a positive result that detects EBOV nucleic acid in a sample, EBOV NP or VP40 positive control assay should be positive with a CT value within 35 cycles for all primer and probe sets. If EBOV NP or VP40 positive controls are negative, the testing results for that plate are invalid. The NTC should be negative. If a NTC is positive, the testing results for that plate are invalid. The HSC (extraction control) should be positive using the RP primer/probe set due to the human DNA in the HSC, and negative with the NP2 or VP40 primer/probe set. A positive result with the HSC and NP2 or VP40 primer/probes would indicate cross-contamination has occurred, and that the testing results for that plate are invalid.

The rRT-PCR control assay using the RP primers and probes on the test sample should be positive (CT<40). If the rRT-PCR RP assay for a test sample is negative and the rRT-PCR assay using the NP2 or VP40 primers and probes for a test sample is negative, then the results of the assay are inconclusive and should be repeated. However, if the rRT-PCR RP assay for a test sample is negative and the rRT-PCR assay using the NP2 or VP40 primers and probes for a test sample is positive, then the test sample should be considered positive for EBOV.

Figure 2:
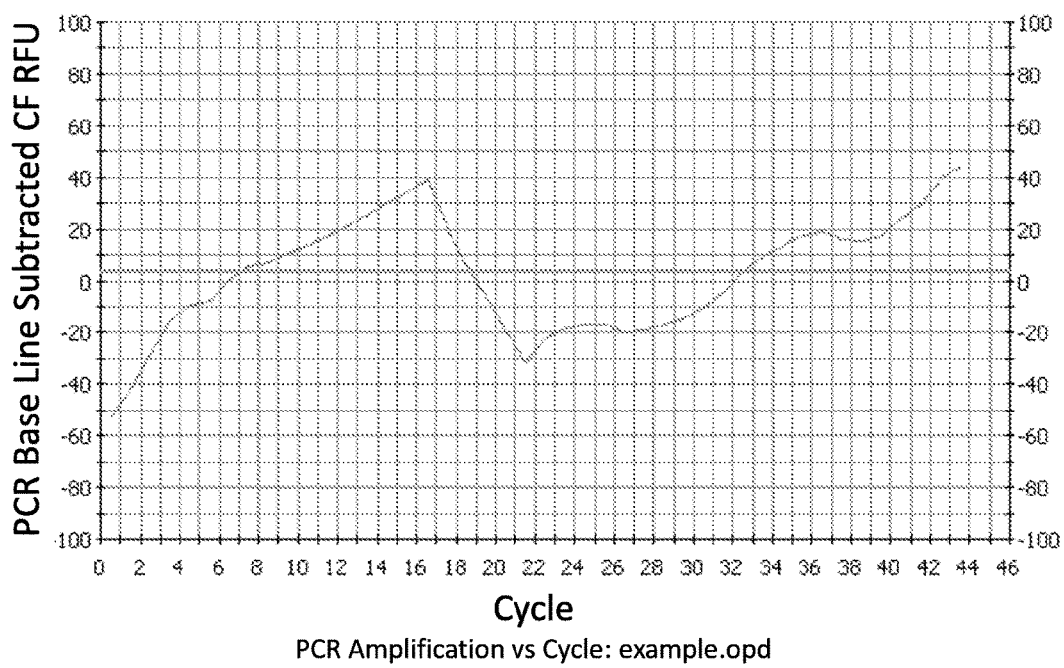
FIG. 2 is a set of graphs showing an example of a false positive RT-PCR amplification curve of EBOV nucleic acid using the VP40 primer and probe set.
Figure 2:
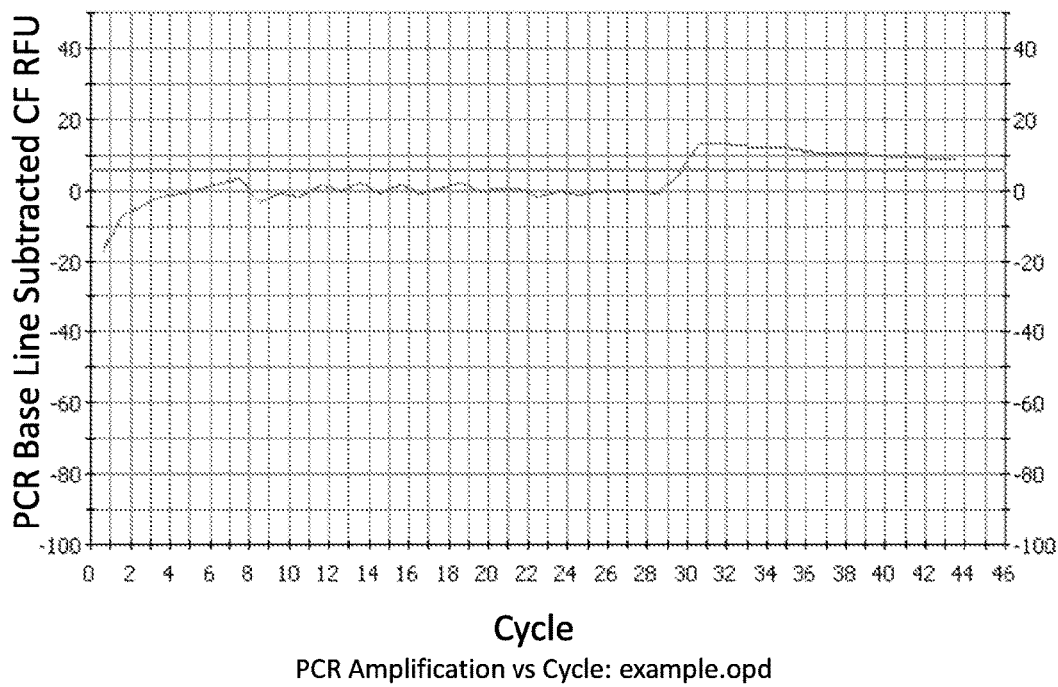

For the test sample assay, true positives should produce exponential curves with logarithmic, linear, and plateau phases (for example, as shown in FIG. 1). Weak positives will produce high CT values that are sometimes devoid of a plateau phase; however the exponential plot will be seen. For a sample to be a true positive, the curve must cross the threshold in a similar fashion as shown in FIG. 1. It should not cross the threshold and then dive back below the threshold. For example, FIG. 2 shows examples of false positives that do not amplify exponentially.

Figure 3:
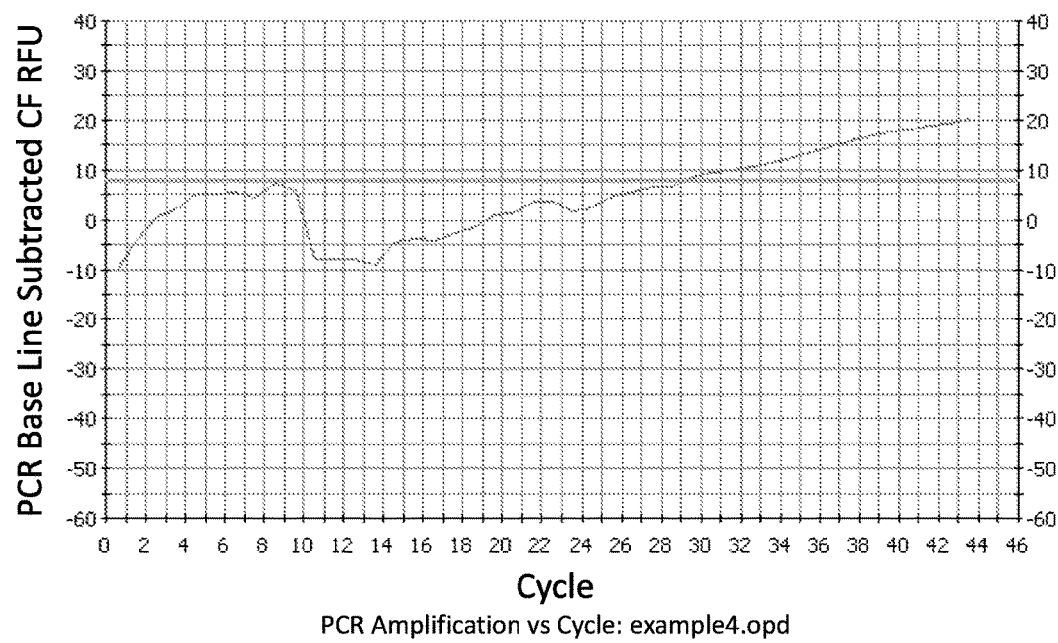
FIG. 3 is a set of graphs showing an RT-PCR amplification curve of an EBOV nucleic acid sample with a "wandering" curve (top) and the corresponding background fluorescence view (bottom) using the VP40 primer and probe set.
Figure 3:
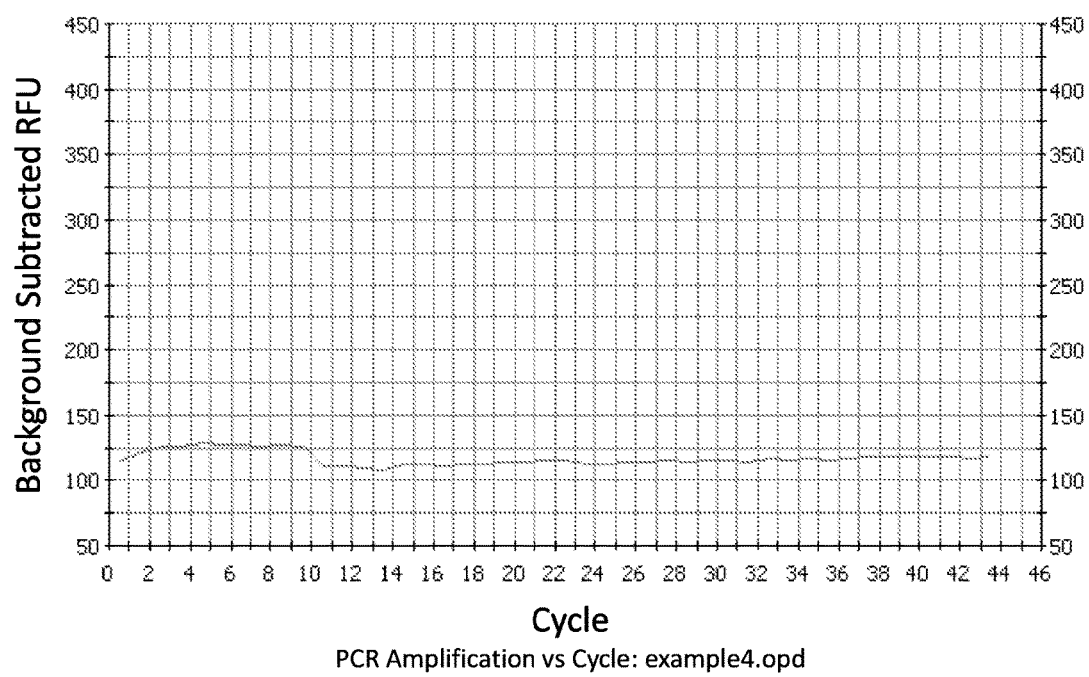
Figure 4:
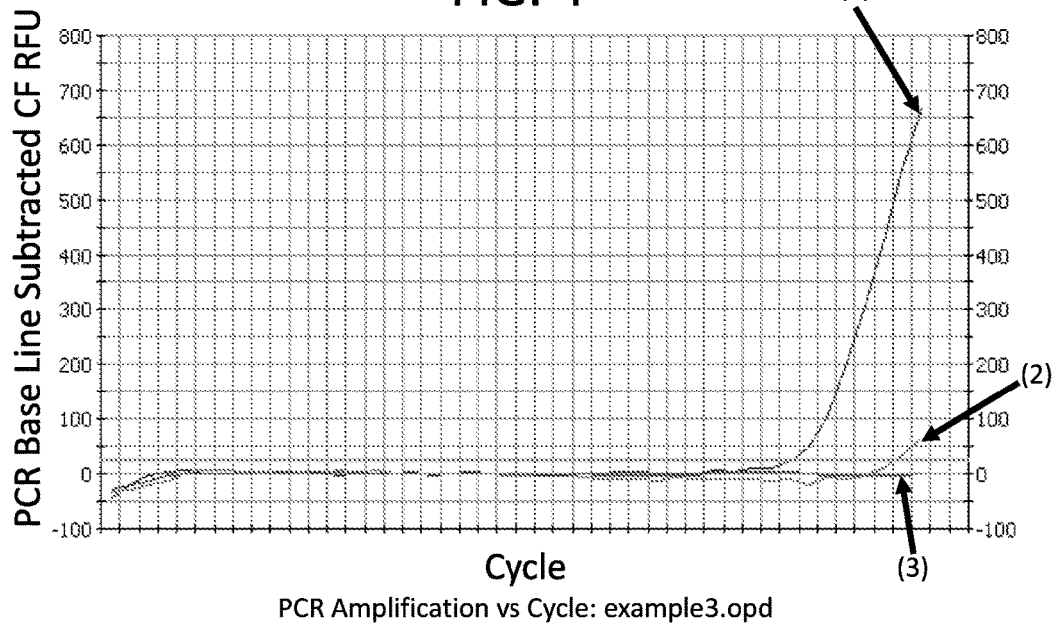
FIG. 4 is a set of graphs showing RT-PCR amplification curves of three EBOV nucleic acid samples in the linear view (top) and the corresponding background fluorescence view (bottom) using the VP40 primer and probe set.
Figure 4:
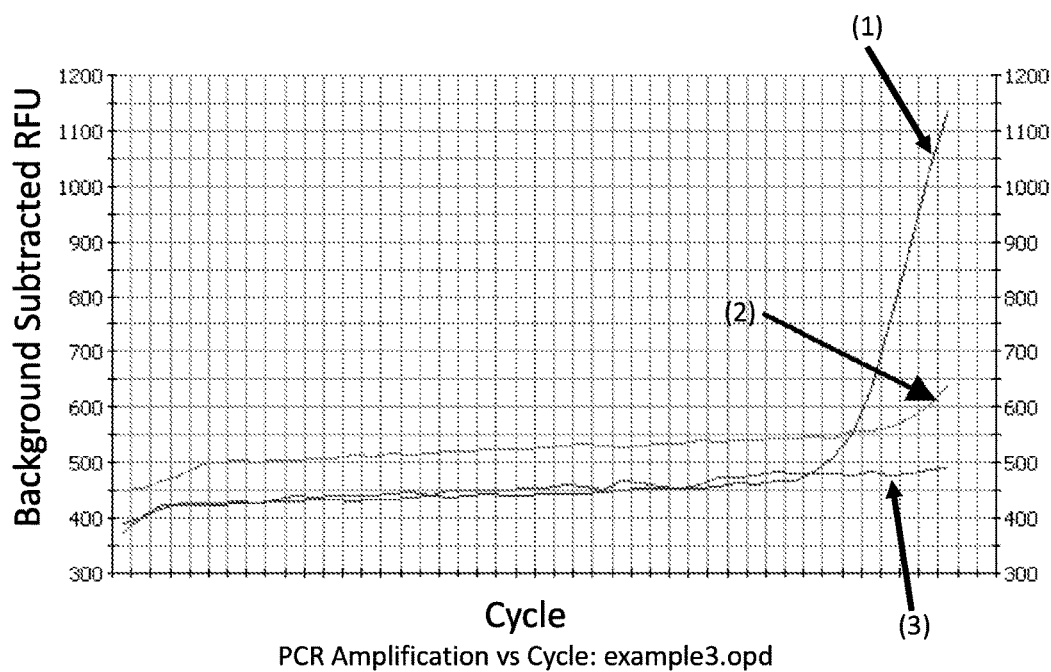

To better understand and evaluate challenging curves more effectively, the background fluorescence of the assay can be analyzed (for example, using the Rn versus Cycle tool with AB software) to determine if the curve reflects a positive test. A sharp increase in background fluorescence indicates a true positive while a flat line (or wandering line) indicates no amplification. FIG. 3 shows a curve with a CT value of 29.2 (top graph) though it is evident that the sample is negative by looking at the background fluorescence view (bottom graph). FIG. 4 shows an amplification plot with 3 curves: a moderately weak positive (curve 1), a very weak positive (curve 2), and a negative control (curve 3) (top graph). The weak positive is verified to be positive by the sharp increase in fluorescence seen in the background fluorescence view (bottom graph).

Figure 5:
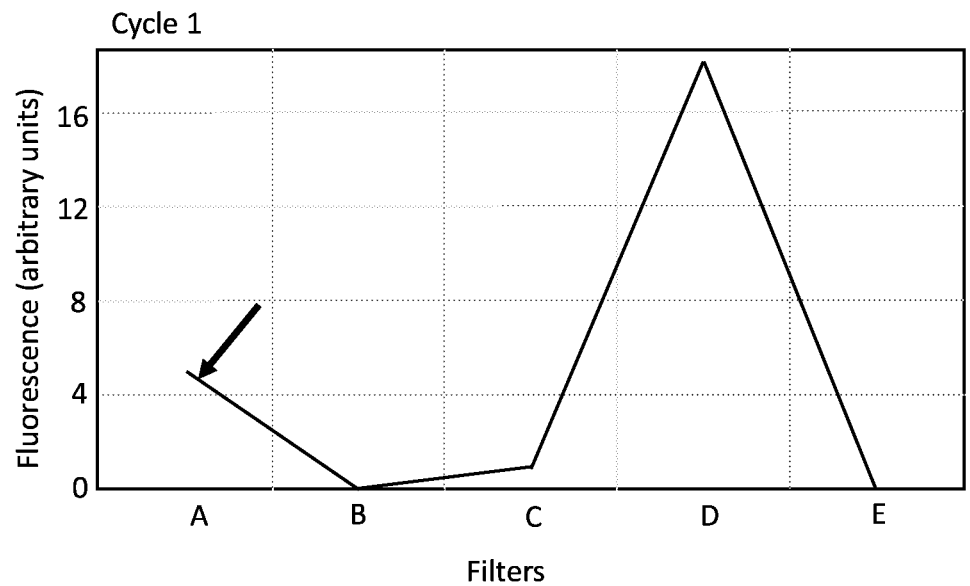
FIG. 5 is a set graphs showing spectra components of a RT-PCR amplification assay on a positive EBOV nucleic acid sample using the VP40 primer and probe. The top graph shows fluorescence at cycle 1 and the bottom graph shows fluorescence at cycle 40.
Figure 5:
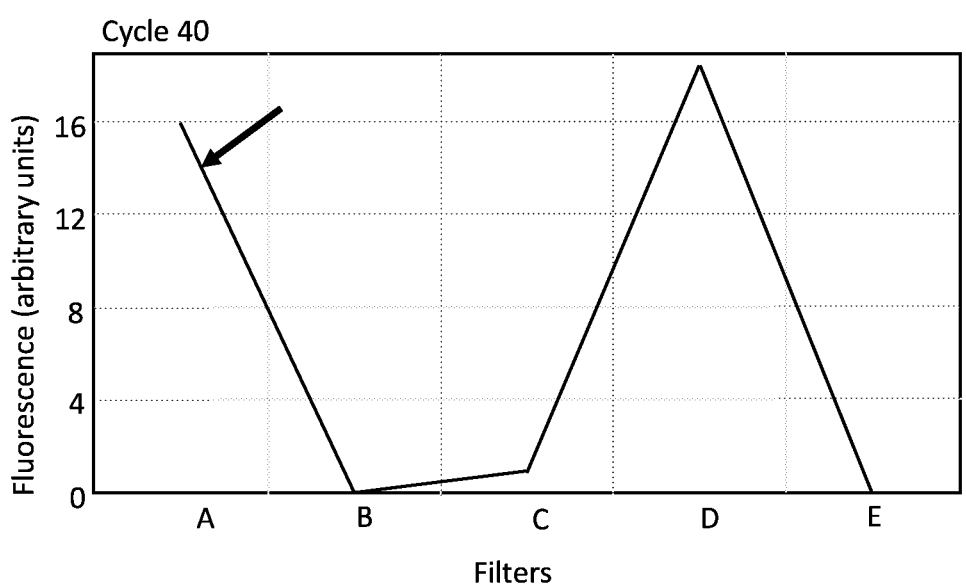

AB software has a spectra component that can be used to evaluate challenging curves more efficiently. The spectra component shows the difference in total fluorescence at every cycle. If there is an obvious difference in the fluorescence from cycle 1 to cycle 38, the sample is a true positive. FIG. 5 shows the spectra view of a positive sample at cycles 1 and 40. Filter A is the FAM filter and indicates if there is an accumulation of fluorescence during the reaction (see arrow). Filter D is the ROX filter and should remain constant.

Weak positive samples (CT≥35) should be interpreted with caution, examined closely and generally repeated. If fluorescence curves are true exponential curves, the reaction should be interpreted as positive.

During convalescence from EBOV infection, the Ct values will be weak and typically do not require repeat testing if all controls react as expected. If repeat testing of a weak specimen is necessary, it is important to repeat the sample in replicates as a single repeat test run has a high likelihood of generating a discrepant result. If re-extracting and re-testing the specimen, it may be helpful to elute in a lower volume to concentrate the sample.

Assay Sensitivity

Limit of Detection—Estimation in PCR Grade Water.

Analytical evaluation of the EBOV VP40 rRT-PCR primer and probe set and the EBOV NP2 rRT-PCR primer and probe set sensitivity across EBOV strains (species EBOV) was performed using three strains: EboZ Mayinga 1976, EboZ Kikwit 1995, and EboZ Gabon 2002. Each strain was prepared in serial dilution in PCR grade water as live virus, extracted and tested. Aliquots of each stock were then inactivated by gamma irradiation, prepared in serial dilution in PCR grade water, extracted and tested. All materials in this study were extracted using a manual method using Tripure inactivation followed by isolation using the Qiagen RNeasy® kit. rRT-PCR was performed using the AB 7500 Fast Dx as described above. The VP40 and NP2 primers and probes performed similarly with live EBOV across all three strains, with an estimated limit of detection (LoD) of approximately 1-3 $TCID_{50}$/reaction (see Tables 1-6). Inactivation by gamma irradiation was demonstrated to impact the sensitivity of the assay. Mayinga and Gabon strains saw 10-fold and 100-fold shifts in estimated LoD, respectively. The Kikwit strain maintained the same estimated LoD (1 or 10 $TCID_{50}$/rxn for VP40 and NP2 assays, respectively), but demonstrated a CT value shift of approximately 2 cycles at that limit concentration.

Inactivated stock of the Mayinga 1976 strain was selected for use in blood and urine limit of detection and contrived specimen testing. Data from the LoD evaluation are presented in Tables 1-6.

TABLE 1

NP2 Analytical Ebola virus sensitivity evaluation (Mayinga 1976)

| $TCID_{50}$/mL | Live virus ($C_T$ values) | | | Inactivated virus ($C_T$ values) | | |
|---|---|---|---|---|---|---|
| $6 \times 10^7$ | 20 | 21 | 20 | 20 | 20 | 20 |
| $6 \times 10^6$ | 24 | 24 | 25 | 26 | 26 | 26 |
| $6 \times 10^5$ | 28 | 28 | 28 | 32 | 32 | 33 |
| $6 \times 10^4$ | 32 | 32 | 32 | 34 | 34 | 34 |
| $6 \times 10^3$ | 35 | 35 | 35 | 39 | und | 38 |
| 600 | 38 | 40 | 39 | und | und | und |
| 60 | und | und | und | und | und | und |
| 6 | und | und | und | und | und | und |
| Neg. Ctrl. | und | und | und | und | und | und |

TABLE 2

NP2 Analytical Ebola virus sensitivity evaluation (Kikwit 1995)

| $TCID_{50}$/mL | Live virus ($C_T$ values) | | | Inactivated virus ($C_T$ values) | | |
|---|---|---|---|---|---|---|
| $2 \times 10^6$ | 22 | 22 | 22 | 23 | 23 | 23 |
| $2 \times 10^5$ | 26 | 26 | 26 | 28 | 29 | 28 |
| $2 \times 10^4$ | 30 | 30 | 30 | 32 | 32 | 32 |
| $2 \times 10^3$ | 33 | 34 | 33 | 35 | 36 | 35 |
| 200 | 39 | 37 | und | und | und | und |
| 20 | und | und | und | und | und | und |
| 2 | und | und | und | und | und | und |
| 0.2 | und | und | und | und | und | und |
| Neg. Ctrl. | und | und | und | und | und | und |

TABLE 3

NP2 Analytical Ebola virus sensitivity evaluation (Gabon 2002)

| $TCID_{50}$/mL | Live virus ($C_T$ values) | | | Inactivated virus ($C_T$ values) | | |
|---|---|---|---|---|---|---|
| $6 \times 10^6$ | 20 | 20 | 21 | 22 | 22 | 22 |
| $6 \times 10^5$ | 24 | 24 | 25 | 27 | 27 | 27 |
| $6 \times 10^4$ | 28 | 28 | 28 | 34 | 34 | 33 |
| $6 \times 10^3$ | 31 | 31 | 32 | 38 | 37 | 37 |
| 600 | 35 | 35 | 35 | und | und | und |
| 60 | und | und | und | und | und | und |
| 6 | und | und | und | und | und | und |
| 0.6 | und | und | und | und | und | und |
| Neg. Ctrl. | und | und | und | und | und | und |

TABLE 4

VP40 Analytical Ebola virus sensitivity evaluation (Mayinga 1976)

| $TCID_{50}$/mL | Live virus ($C_T$ values) | | | Inactivated virus ($C_T$ values) | | |
|---|---|---|---|---|---|---|
| $6 \times 10^7$ | 18 | 18 | 18 | 18 | 18 | 18 |
| $6 \times 10^6$ | 22 | 22 | 22 | 24 | 24 | 24 |
| $6 \times 10^5$ | 25 | 25 | 25 | 30 | 30 | 30 |
| $6 \times 10^4$ | 29 | 29 | 29 | 31 | 31 | 32 |
| $6 \times 10^3$ | 32 | 32 | 32 | 35 | 36 | 36 |
| 600 | 35 | 35 | 35 | 38 | 39 | 39 |

TABLE 4-continued

VP40 Analytical Ebola virus sensitivity evaluation (Mayinga 1976)

| $TCID_{50}$/mL | Live virus ($C_T$ values) | | | Inactivated virus ($C_T$ values) | | |
|---|---|---|---|---|---|---|
| 60 | 39 | 38 | 38 | und | und | und |
| 6 | und | und | und | und | und | und |
| Neg. Ctrl. | und | und | und | und | und | und |

TABLE 5

VP40 Analytical Ebola virus sensitivity evaluation (Kikwit 1995)

| $TCID_{50}$/mL | Live virus ($C_T$ values) | | | Inactivated virus ($C_T$ values) | | |
|---|---|---|---|---|---|---|
| $2 \times 10^6$ | 20 | 20 | 20 | 22 | 21 | 21 |
| $2 \times 10^5$ | 24 | 24 | 24 | 26 | 26 | 26 |
| $2 \times 10^4$ | 27 | 27 | 27 | 28 | 29 | 28 |
| $2 \times 10^3$ | 31 | 31 | 31 | 32 | 33 | 33 |
| 200 | 34 | 34 | 34 | 35 | 37 | 36 |
| 20 | 38 | 37 | 38 | 40 | 39 | 37 |
| 2 | und | und | und | und | und | und |
| 0.2 | und | und | und | und | und | und |
| Neg. Ctrl. | und | und | und | und | und | und |

TABLE 6

VP40 Analytical Ebola virus sensitivity evaluation (Gabon 2002)

| $TCID_{50}$/mL | Live virus ($C_T$ values) | | | Inactivated virus ($C_T$ values) | | |
|---|---|---|---|---|---|---|
| $6 \times 10^6$ | 19 | 18 | 18 | 21 | 21 | 21 |
| $6 \times 10^5$ | 22 | 22 | 22 | 25 | 25 | 25 |
| $6 \times 10^4$ | 26 | 26 | 26 | 31 | 31 | 31 |
| $6 \times 10^3$ | 29 | 29 | 29 | 35 | 35 | 35 |
| 600 | 33 | 33 | 33 | 32 | 32 | 32 |
| 60 | 36 | 36 | 36 | und | und | 39 |
| 6 | und | 40 | und | und | und | und |
| 0.6 | und | Und | und | und | und | und |
| Neg. Ctrl. | und | Und | und | und | und | und |

Limit of Detection—Confirmation in Whole Blood

The limit of detection of EBOV VP40 and NP2 rRT-PCR primer and probe sets in whole blood was confirmed to be 600 $TCID_{50}$/reaction. The limit of detection was determined by testing four pools of spiked whole blood. Each of the four pools was spiked with inactivated EBOV (Mayinga 1976) at a different concentration ($6 \times 10^4$ $TCID_{50}$/rxn, $6 \times 10^3$ $TCID_{50}$/rxn, 600 $TCID_{50}$/rxn, and 60 $TCID_{50}$/rxn).

Each pool was extracted 20 times using the Dynal Bead-Retriever® (Life Technologies, catalog #159-50) protocol with the MagMAX® extraction kit (Life Technologies, Cat #4462359). Each extract was used as template for rRT-PCR assays using the VP40 and NP2 primers and probes as described above. Results from the VP40 and NP2 rRT-PCR assays, and a control rRT-PCR using Primers and probe specific for RNAse P nucleic acid, are presented in Tables 7-9.

TABLE 7

Limit of detection in whole blood - VP40 data

| $TCID_{50}$/mL | VP40 assay $C_T$ values | | | | | | | | | |
|---|---|---|---|---|---|---|---|---|---|---|
| $6 \times 10^4$ | 30 | 29 | 29 | 29 | 29 | 29 | 29 | 29 | 29 | 28 |
| | 29 | 28 | 28 | 28 | 28 | 28 | 28 | 28 | 28 | 29 |
| $6 \times 10^3$ | 33 | 33 | 33 | 33 | 33 | 32 | 32 | 32 | 33 | 33 |
| | 33 | 33 | 32 | 32 | 32 | 31 | 32 | 33 | 32 | 32 |
| 600 | 38 | 37 | 35 | 37 | 36 | 36 | 35 | 35 | 38 | 36 |
| | 36 | 36 | 36 | 36 | 35 | 35 | 35 | 35 | 35 | 35 |

TABLE 7-continued

Limit of detection in whole blood - VP40 data

| TCID$_{50}$/mL | VP40 assay $C_T$ values | | | | | | | | | |
|---|---|---|---|---|---|---|---|---|---|---|
| 60 | 40 | 40 | 39 | 40 | Und | 38 | 39 | und | und | und |
|  | 40 | 35 | und | 38 | 38 | 40 | 38 | 38 | 38 | und |
| Neg. Ctrl. | und | und | und | und | | | | | | |

TABLE 8

Limit of detection in whole blood - NP2 data

| TCID$_{50}$/mL | NP2 assay $C_T$ values | | | | | | | | | |
|---|---|---|---|---|---|---|---|---|---|---|
| 6 × 10$^4$ | 31 | 32 | 34 | 30 | 31 | 30 | 31 | 30 | 32 | 29 |
|  | 30 | 30 | 30 | 30 | 30 | 29 | 30 | 30 | 30 | 30 |
| 6 × 10$^3$ | 33 | 36 | 34 | 35 | 35 | 34 | 34 | 33 | 36 | 34 |
|  | 34 | 35 | 33 | 35 | 34 | 33 | 35 | 34 | 34 | 35 |
| 600 | und | und | 39 | und | und | und | und | und | und | und |
|  | und | 39 | und | und | und | und | und | 40 | und | und |
| 60 | und | und | und | und | und | und | und | und | und | und |
|  | und | und | und | und | und | und | und | und | und | und |
| Neg. Ctrl. | und | und | und | und | | | | | | |

TABLE 9

Limit of detection in whole blood - RP data

| TCID$_{50}$/mL | RP assay $C_T$ values | | | | | | | | | |
|---|---|---|---|---|---|---|---|---|---|---|
| 6 × 10$^4$ | 25 | 25 | 25 | 25 | 25 | 24 | 24 | 25 | 25 | 25 |
|  | 25 | 25 | 25 | 25 | 25 | 24 | 24 | 25 | 25 | 25 |
| 6 × 10$^3$ | 24 | 25 | 25 | 25 | 25 | 24 | 24 | 24 | 24 | 24 |
|  | 26 | 26 | 24 | 25 | 25 | 24 | 24 | 25 | 25 | 24 |
| 600 | 24 | 25 | 24 | 25 | 25 | 25 | 24 | 24 | 24 | 24 |
|  | 25 | 25 | 24 | 25 | 25 | 25 | 24 | 24 | 24 | 24 |
| 60 | 25 | 25 | 26 | 25 | 25 | 25 | 24 | 24 | 23 | 25 |
|  | 26 | 25 | 25 | 25 | 25 | 25 | 25 | 24 | 25 | 24 |
| Neg. Ctrl. | und | und | und | und | | | | | | |

Limit of Detection—Confirmation in Urine

The limit of detection of EBOV VP40 and NP2 rRT-PCR primer and probe sets in whole blood was confirmed to be 30 TCID$_{50}$/reaction. The limit of detection was determined by testing four pools of spiked urine. Each of the four pools was spiked with inactivated EBOV (Mayinga 1976) at a different concentration (6×10$^4$ TCID$_{50}$/rxn, 6×10$^3$ TCID$_{50}$/rxn, 600 TCID$_{50}$/rxn, and 60 TCID$_{50}$/rxn). Each pool was extracted 20 times using the Dynal BeadRetriever® (Life Technologies, catalog #159-50) protocol with the Mag-MAX® extraction kit (Life Technologies, Cat #4462359). Each extract was used as template for rRT-PCR assays using the VP40 and NP2 primers and probes as described above. Results from the VP40 and NP2 rRT-PCR assays, and a control rRT-PCR using Primers and probe specific for RNAse P nucleic acid, are presented in Tables 10-12.

TABLE 10

Limit of detection in urine - VP40 data

| TCID$_{50}$/mL | VP40 assay $C_T$ values | | | | | | | | | |
|---|---|---|---|---|---|---|---|---|---|---|
| 6 × 10$^4$ | 28 | 32 | 30 | 30 | 31 | 30 | 31 | 30 | 31 | 30 |
|  | 28 | 27 | 29 | 28 | 30 | 28 | 29 | 29 | 28 | 30 |
| 6 × 10$^3$ | 30 | 30 | 30 | 30 | 31 | 30 | 30 | 33 | 33 | 35 |
|  | 33 | 34 | 34 | 34 | 34 | 35 | 35 | 34 | 35 | 35 |
| 600 | 35 | 37 | 36 | 37 | 38 | 37 | 36 | 37 | 36 | 37 |
|  | 39 | 37 | 36 | 36 | 36 | 37 | 36 | 36 | 36 | 36 |
| 60 | Und | 38 | Und | und | 38 | und | und | und | 38 | 38 |
|  | 38 | 38 | 38 | und | 38 | 39 | und | und | und | 38 |
| Neg. Ctrl. | und | Und | und | und | | | | | | |

TABLE 11

Limit of detection in urine - NP2 data

| TCID$_{50}$/mL | NP2 assay $C_T$ values | | | | | | | | | |
|---|---|---|---|---|---|---|---|---|---|---|
| 6 × 10$^4$ | 29 | 31 | 29 | 29 | 31 | 30 | 30 | 29 | 31 | 30 |
|  | 28 | 28 | 28 | 28 | 28 | 28 | 28 | 28 | 28 | 29 |
| 6 × 10$^3$ | 32 | 31 | 31 | 31 | 31 | 31 | 31 | 32 | 32 | 34 |
|  | 32 | 33 | 33 | 32 | 31 | 34 | 33 | 33 | 33 | 34 |

TABLE 11-continued

Limit of detection in urine - NP2 data

| TCID$_{50}$/mL | NP2 assay C$_T$ values | | | | | | | | | |
|---|---|---|---|---|---|---|---|---|---|---|
| 600 | 38 | 39 | 38 | 38 | 39 | 38 | 38 | und | und | 38 |
|  | 39 | 38 | 38 | 37 | 39 | 37 | 38 | 39 | 38 | 38 |
| 60 | und | 40 | 40 | und | 38 | 40 | 37 | und | und | 38 |
|  | 38 | 39 | 39 | und | 40 | und | und | und | und | und |
| Neg. Ctrl. | und | und | und | und | | | | | | |

TABLE 12

Limit of detection in urine - RP data

| TCID$_{50}$/mL | RP assay C$_T$ values | | | | | | | | | |
|---|---|---|---|---|---|---|---|---|---|---|
| 6 × 10$^4$ | 36 | 36 | 36 | 36 | 34 | 36 | 36 | 35 | 36 | 36 |
|  | 38 | 35 | 35 | 36 | 35 | 36 | 38 | 35 | 35 | 35 |
| 6 × 10$^3$ | 36 | 36 | 36 | 35 | 35 | 36 | 36 | 35 | 35 | 35 |
|  | 37 | 35 | 36 | 35 | 35 | 37 | 36 | 35 | 35 | 38 |
| 600 | 35 | 36 | 35 | 35 | 35 | 35 | 34 | 35 | 35 | 35 |
|  | 35 | 36 | 35 | 36 | 35 | 36 | 35 | 36 | 35 | 36 |
| 60 | 34 | 35 | 36 | 34 | 35 | 35 | 34 | 35 | 35 | 35 |
|  | 36 | 35 | 35 | 36 | 35 | 35 | 36 | 35 | 35 | 35 |
| Neg. Ctrl. | und | und | und | und | | | | | | |

Analytical Reactivity Evaluation—in Silico Analysis

In silico analysis of EBOV VP40 rRT-PCR Assay primer and probe sequences and EBOV NP2 rRT-PCR Assay primer and probe sequences was performed to verify reagent sequence homology with the target region of five current and eight historical Ebola outbreak strains. All primer and probe sequences showed 100% alignment, predicting no false negative results are likely to occur. The following table provides a summary of the findings.

TABLE 13

In Silico Reactivity based on sequence identity

| Strain | GenBank # | Primer/Probe Sequence Identity | | | Primer/Probe Sequence Identity | | |
|---|---|---|---|---|---|---|---|
|  |  | VP40-F | VP40-R | VP40-P | VP40-F | VP40-R | VP40-P |
| Liberia 2014 |  | 100% | 100% | 100% | 100% | 100% | 100% |
| SierraLeone 2014 | KM233053 | 100% | 100% | 100% | 100% | 100% | 100% |
| SierraLeone 2014 | KM233035 | 100% | 100% | 100% | 100% | 100% | 100% |
| Guinea 2014 | KJ660347 | 100% | 100% | 100% | 100% | 100% | 100% |
| Guinea 2014 | KJ660346 | 100% | 100% | 100% | 100% | 100% | 100% |
| DRC Luebo 2007 | KC242788 | 100% | 100% | 100% | 100% | 100% | 100% |
| DRC Luebo 2007 | KC242784 | 100% | 100% | 100% | 100% | 100% | 100% |
| Gabon 1996 | KC242793 | 100% | 100% | 100% | 100% | 100% | 100% |
| Gabon 1996 | KC242794 | 100% | 100% | 100% | 100% | 100% | 100% |
| DRC Kikwit 1995 | AY354458 | 100% | 100% | 100% | 100% | 100% | 100% |
| DRC Kikwit 1995 | KC242796 | 100% | 100% | 100% | 100% | 100% | 100% |
| DRC Mayinga 1976 | KC242791 | 100% | 100% | 100% | 100% | 100% | 100% |
| DRC Mayinga 1976 | NC_002549 | 100% | 100% | 100% | 100% | 100% | 100% |

Analytical Specificity

The EBOV VP40 rRT-PCR primer and probe set and the EBOV NP2 rRT-PCR primer and probe set were assayed for specificity for EBOV, and found to be 100% specific. Specificity was evaluated through testing of a set of near neighbor viruses. Each live virus was prepared at a concentration of 10$^5$ TCID$_{50}$/mL, extracted and tested using the AB 7500 Fast Dx and assayed in quadruplicate by rRT-PCR using the VP40 primers and probe and the NP2 primers and probe as described above. A positive control (EBOV Mayinga 1976) and a negative extraction control were also tested. Tables 14 and 15 provide a summary of the findings.

TABLE 14

VP40 specificity

| Virus | VP40 Results (C$_T$ values) | | | |
|---|---|---|---|---|
|  | Replicate 1 | Replicate 2 | Replicate 3 | Replicate 4 |
| EBOV Mayinga 1976 | 25 | 25 | 25 | 25 |
| Neg. control. | Und | und | und | und |
| Sudan virus | Und | und | und | und |
| Bundibugyo | Und | und | und | und |
| Reston Ebolavirus | Und | und | und | und |
| Taï Forest virus | Und | und | und | und |
| Marburg virus | Und | und | und | und |
| RAVN Marburgvirus | Und | und | und | und |
| Rift Valley Fever virus | Und | und | und | und |
| Crimean Congo Hemorrhagic Fever virus | Und | und | und | und |
| Lassa virus | Und | und | und | und |

TABLE 15

NP2 specificity

| Virus | NP2 Results (C$_T$ values) | | | |
|---|---|---|---|---|
|  | Replicate 1 | Replicate 1 | Replicate 1 | Replicate 1 |
| EboZ Mayinga 1976 | 26 | 26 | 27 | 27 |
| Neg. ctrl. | Und | und | und | und |
| Sudan virus | Und | und | und | und |
| Bundibugyo | Und | und | und | und |
| Reston Ebolavirus | Und | und | und | und |

TABLE 15-continued

NP2 specificity

NP2 Results ($C_T$ values)

| Virus | Replicate 1 | Replicate 1 | Replicate 1 | Replicate 1 |
|---|---|---|---|---|
| Taï Forest virus | Und | und | und | und |
| Marburg virus | Und | und | und | und |
| RAVN Marburgvirus | Und | und | und | und |
| Rift Valley Fever virus | Und | und | und | und |
| Crimean Congo Hemorrhagic Fever virus | Und | und | und | und |
| Lassa virus | Und | und | und | und |

Additional evaluation of the analytical specificity of EBOV VP40 rRT-PCR and EBOV NP2 rRT-PCR was performed through in silico analysis of the VP40 and NP2 rRT-PCR primer and probe sequences against other common causes of fever in persons returning from Africa as well as hemorrhagic fever-causing viruses. BLASTn analysis queries of the these primers and probe sequences were performed against the GenBank public domain nucleotide sequences and showed no significant combined homologies (primer target and probe target) with sequences from the other conditions that would predict potential false positive rRT-PCR results. Conditions and associated causative agents covered in the in silico specificity analysis are presented in Table 16.

TABLE 16

In silico Specificity

| Disease/condition | Organism (taxid) | Agent |
|---|---|---|
| Malaria | 5883 | Plasmodium falciparum |
| Typhoid Fever | 90370 | Salmonella typhi |
| Meningococcal disease | 487 | Neisseria meningitidis |
| Pneumonia | 1313 | Streptococcus pneumoniae |
| Pneumonia | 727 | Hemophilus influenzae |
| Dengue | 12637 | Dengue virus |
| African trypanosomiasis | 31285 | Trypanosoma brucei gambiense |
| Tickborne rickettsiae | 782 | Rickettsia prowazekii |
| Tickborne rickettsiae | 785 | Rickettsia typhi |
| Tickborne rickettsiae | 781 | Rickettsia conorii |
| Tickborne rickettsiae | 35788 | Rickettsia africae |
| Acute schistosomasis | 6183 | Schistosoma mansoni |
| Acute schistosomasis | 6187 | Schistosoma intercalatum |
| Acute schistosomasis | 6185 | Schistosoma heamatobium |
| Influenza | 197911 | Influenzavirus A |
| Influenza | 197912 | Influenzavirus B |
| Leptospirosis | 171 | Leptospira genus |
| Lassa Fever | 11620 | Lassa virus |
| VHF | 11269 | Marburg virus |
| VHF | 186539 | Reston virus |
| VHF | 186540 | Sudan virus |
| VHF | 565995 | Bundibugyo virus |
| VHF | 186541 | Taï Forest virus |
| VHF | 11593 | Crimean Congo Hemorrhagic Fever |

Contrived Clinical Specimen Studies
Contrived Whole Blood (EDTA)

Clinical evaluation of the VP40 and NP2 rRT-PCR primer and probe sets was performed using the Mayinga 1976 strain of species *Zaire ebolavirus*. Whole blood (EDTA) specimens from 50 donors were separated into two 100 µL, aliquots. One 100 µL aliquot was left neat (no virus added) and the other 100 µL, aliquot was spiked with either a low concentration ($2\times10^4$ $TCID_{50}$/mL) or high concentration ($2\times10^5$ $TCID_{50}$/mL) of inactivated EBOV. These 100 specimens were then blinded and passed off for testing to a technician not involved in specimen preparation. Each specimen was extracted using the Dynal BeadRetriever® instrument, and tested using the AB 7500 Fast Dx as described above. A summary of the data generated is presented in Tables 17 and 18 (showing VP40 and NP2 assay results, respectively). No erroneous results were obtained.

TABLE 17

VP40 Contrived Whole Blood (EDTA) Specimens: Summary of Results

| $TCID_{50}$/mL | Total # | Positive | Inclusive | Negative |
|---|---|---|---|---|
| Low Concentration ($2 \times 10^4$ $TCID_{50}$/mL) | 25 | 25 | 0 | 0 |
| High Concentration ($2 \times 10^5$ $TCID_{50}$/mL) | 25 | 25 | 0 | 0 |
| No Virus Added | 50 | 0 | 0 | 50 |

Positive percentage agreement: 100% (50/50) (95% CI: 93%, 100%)

Negative percentage agreement: 100% (50/50) (95% CI: 93%, 100%)

TABLE 18

NP2 Contrived Whole Blood (EDTA) Specimens: Summary of Results

| $TCID_{50}$/mL | Total # | Positive | Inclusive | Negative |
|---|---|---|---|---|
| Low Concentration ($2 \times 10^4$ $TCID_{50}$/mL) | 25 | 25 | 0 | 0 |
| High Concentration ($2 \times 10^5$ $TCID_{50}$/mL) | 25 | 25 | 0 | 0 |
| No Virus Added | 50 | 0 | 0 | 50 |

Positive percentage agreement: 100% (50/50) (95% CI: 93%, 100%)
Negative percentage agreement: 100% (50/50) (95% CI: 93%, 100%)

Contrived Urine Specimens

Clinical evaluation of the VP40 and NP2 rRT-PCR primer and probe sets was performed using the Mayinga 1976 strain of species *Zaire ebolavirus*. Urine specimens from 50 febrile pediatric patients were separated into two 100 µL, aliquots. One 100 µL aliquot was left neat (no virus added) and the other 100 µL, aliquot was spiked with either a low concentration ($2\times10^4$ $TCID_{50}$/mL) or high concentration ($2\times10^5$ $TCID_{50}$/mL) of inactivated EBOV. These 100 specimens were then blinded and passed off for testing to a technician not involved in specimen preparation. Each specimen was extracted using the Dynal BeadRetriever® instrument, and tested using the AB 7500 Fast Dx as described above. A summary of the data generated is presented in Tables 19 and 20 (showing VP40 and NP2 assay results, respectively). No erroneous results were obtained.

TABLE 19

VP40 Contrived Urine Specimens: Summary of Results

| $TCID_{50}$/mL | Total # | Positive | Inclusive | Negative |
|---|---|---|---|---|
| Low Concentration ($2 \times 10^4$ $TCID_{50}$/mL) | 25 | 25 | 0 | 0 |
| High Concentration ($2 \times 10^5$ $TCID_{50}$/mL) | 25 | 25 | 0 | 0 |
| No Virus Added | 50 | 3 | 1 | 46 |

Positive percentage agreement: 100% (50/50) (95% CI: 93%, 100%)
Negative percentage agreement: 93.9% (46/49) (95% CI: 83%, 98%)

TABLE 20

NP2 Contrived Urine Specimens: Summary of Results

| $TCID_{50}/mL$ | Total # | Positive | Inclusive | Negative |
|---|---|---|---|---|
| Low Concentration ($2 \times 10^4$ $TCID_{50}/mL$) | 25 | 25 | 0 | 0 |
| High Concentration ($2 \times 10^5$ $TCID_{50}/mL$) | 25 | 25 | 0 | 0 |
| No Virus Added | 50 | 0 | 1 | 49 |

Positive percentage agreement: 98% (49/50) (95% CI: 90%, 100%)
Negative percentage agreement: 100% (49/49) (95% CI: 93%, 100%)

Bio-Rad CFX96 Bridging Study
CFX96 Bridging Study—LoD Estimation in Whole Blood

A stock of Ebola virus prepared from a strain obtained in the outbreak in West Africa (Liberia 2014) was quantified and then inactivated by gamma irradiation. Serial 10-fold dilutions of this quantified inactivated stock was prepared in whole blood and extracted according to the Dynal Bead-Retriever® (Life Technologies, catalog #159-50) protocol with the MagMAX® extraction kit (Life Technologies, Cat #4462359). Each dilution was then tested side-by-side in duplicate using the VP40 primer and probe set or the NP2 primer and probe set on both the AB 7500 Fast Dx and the Bio-Rad CFX96. Results of this testing are presented in Tables 21 and 22, and show that both the AB 7500 Fast Dx and the Bio-Rad CFX96 rt-PCR systems can be used to detect ebola virus nucleic acids in a sample.

TABLE 21

VP40 7500 Fast DX and CFX96 Side-by-Side Serial Dilution Data

| Ebola virus (Liberia 2014) | | VP40 $C_T$ values (Duplicate testing) | | | |
|---|---|---|---|---|---|
| Dilution | $TCID_{50}/mL$ | AB 7500 Fast Dx | | Bio-Rad CFX96 Touch | |
| −1 | 40,000,000 | 19 | 20 | 19 | 19 |
| −2 | 4,000,000 | 23 | 23 | 22 | 22 |
| −3 | 400,000 | 27 | 27 | 26 | 26 |
| −4 | 40,000 | 29 | 30 | 28 | 28 |
| −5 | 4,000 | 33 | 33 | 33 | 32 |
| −6 | 400 | 37 | 36 | 36 | 36 |
| −7 | 40 | Und | und | und | 39 |
| −8 | 4 | Und | und | und | und |
| Neg. Ctrl. | 0 | Und | und | und | und |

TABLE 22

NP2 7500 Fast DX and CFX96 Side-by-Side Serial Dilution Data

| Ebola virus (Liberia 2014) | | NP2 $C_T$ values (Duplicate testing) | | | |
|---|---|---|---|---|---|
| Dilution | $TCID_{50}/mL$ | AB 7500 Fast Dx | | Bio-Rad CFX96 Touch | |
| −1 | 40,000,000 | 20 | 20 | 20 | 20 |
| −2 | 4,000,000 | 24 | 24 | 23 | 23 |
| −3 | 400,000 | 28 | 28 | 27 | 27 |
| −4 | 40,000 | 30 | 30 | 30 | 30 |
| −5 | 4,000 | 34 | 34 | 34 | 33 |
| −6 | 400 | 37 | 38 | 39 | 37 |
| −7 | 40 | Und | und | und | und |
| −8 | 4 | Und | und | und | und |
| Neg. Ctrl. | 0 | Und | und | und | und |

CFX96 Bridging Study—LoD Verification in Whole Blood

The lowest concentration generating 100% positive results in the initial range-finding step (400 $TCID_{50}/mL$) was tested a further 20 times on each PCR instrument to verify the limit of detection using the VP40 primer and probe set or the NP2 primer and probe set. These data are presented in Tables 23 and 24.

TABLE 23

VP40 7500 Fast Dx and CFX96 Side-by-Side Limit of Detection Verification

| Instrument | VP40 $C_T$ values - Replicate testing (400 $TCID_{50}/mL$) | | | | | | | | | | Negative Control |
|---|---|---|---|---|---|---|---|---|---|---|---|
| AB 7500 Fast Dx | 35 | 35 | 35 | 34 | 35 | 35 | 35 | 35 | 34 | 35 | und |
|  | 35 | 35 | 35 | 35 | 34 | 35 | 34 | 34 | 35 | 35 | |
| Bio-Rad CFX96 Touch | 35 | 34 | 35 | 35 | 35 | 34 | 35 | 35 | 35 | 35 | und |
|  | 35 | 35 | 36 | 35 | 35 | 33 | 35 | 36 | 35 | 35 | |

TABLE 24

NP2 7500 Fast Dx and CFX96 Side-by-Side Limit of Detection Verification

| Instrument | NP2 $C_T$ values - Replicate testing (400 $TCID_{50}/mL$) | | | | | | | | | | Negative Control |
|---|---|---|---|---|---|---|---|---|---|---|---|
| AB 7500 Fast Dx | 36 | 35 | 35 | 35 | 35 | 35 | 36 | 35 | 35 | 35 | und |
|  | 35 | 35 | 36 | 35 | 35 | 36 | 35 | 36 | 36 | 35 | |
| Bio-Rad CFX96 Touch | 37 | 37 | 37 | 37 | 37 | 37 | 37 | 37 | 37 | 37 | und |
|  | 36 | 37 | 37 | 37 | 37 | 36 | 36 | 37 | 37 | 36 | |

The limit of detection for both the CFX96 and the AB 7500 Fast Dx in this evaluation is 400 $TCID_{50}/mL$. These data suggest that the performance of the CFX96 is comparable to the performance of the AB7500 Fast Dx with this assay.

Extraction Instrument Bridging Study
MagMAX Express-96 Deep Well Magnetic Particle Processor—Side-by-side Serial Dilution Testing A stock of Ebola virus prepared from a strain obtained in the outbreak in West Africa (Liberia 2014) was quantified and then inactivated by gamma irradiation. Serial 10-fold dilutions of the quantified, inactivated stock was prepared in whole blood. Each concentration was extracted three times by each extraction method: the MagMAX Pathogen RNA/DNA Kit on the Dynal BeadRetriever and the same extraction kit on the MagMAX Express-96 Deep Well Magnetic Particle Processor (Life Technologies, catalog #4400079). Resulting nucleic acid samples were tested once by EBOV VP40 rRT-PCR and once by EBOV NP2 rRT-PCR. Data demonstrate comparable performance between the two automated extraction instruments. Results of this evaluation are presented in Table 25 (VP40), Table 26 (NP2) and Table 27 (RP). The results show that both the MagMAX Pathogen RNA/DNA Kit and MagMAX Express-96 Deep Well Magnetic Particle Processor can be used in the disclosed assays.

TABLE 25

Dynal BeadRetriever ® and MagMAX ® Express-96 Side-by-side VP40 Serial Dilution Data

| Ebola virus (Liberia 2014) | | VP40 $C_T$ values (Duplicate testing) | | | | | |
|---|---|---|---|---|---|---|---|
| Dilution | $TCID_{50}/mL$ | AB 7500 Fast Dx | | | Bio-Rad CFX96 Touch | | |
| −2 | 4,000,000 | 25 | 24 | 24 | 24 | 24 | 24 |
| −3 | 400,000 | 27 | 27 | 27 | 27 | 27 | 27 |
| −4 | 40,000 | 31 | 31 | 30 | 30 | 30 | 30 |
| −5 | 4,000 | 34 | 35 | 34 | und | 34 | 34 |

TABLE 25-continued

Dynal BeadRetriever® and MagMAX® Express-96
Side-by-side VP40 Serial Dilution Data

| Ebola virus (Liberia 2014) | | VP40 $C_T$ values (Duplicate testing) | | | | |
|---|---|---|---|---|---|---|
| Dilution | TCID$_{50}$/mL | AB 7500 Fast Dx | | | Bio-Rad CFX96 Touch | |
| −6 | 400 | 38 | 38 | und | 38 | und | 36 |
| HSC | 0 | und | und | und | und | und | und |

TABLE 26

Dynal BeadRetriever® and MagMAX® Express-96
Side-by-side NP2 Serial Dilution Data

| Ebola virus (Liberia 2014) | | NP2 $C_T$ values (Duplicate testing) | | | | | |
|---|---|---|---|---|---|---|---|
| Dilution | TCID$_{50}$/mL | AB 7500 Fast Dx | | | Bio-Rad CFX96 Touch | | |
| −2 | 4,000,000 | 26 | 25 | 25 | 25 | 25 | 25 |
| −3 | 400,000 | 28 | 28 | 28 | 28 | 28 | 28 |
| −4 | 40,000 | 31 | 32 | 31 | 31 | 32 | 31 |
| −5 | 4,000 | 35 | 35 | 35 | und | 35 | 35 |
| −6 | 400 | und | und | und | und | 38 | 39 |
| HSC | 0 | und | und | und | und | und | und |

TABLE 27

Dynal BeadRetriever® and MagMAX® Express-96
Side-by-side RP Serial Dilution Data

| Ebola virus (Liberia 2014) | | RP $C_T$ values Duplicate testing) | | | | | |
|---|---|---|---|---|---|---|---|
| Dilution | TCID$_{50}$/mL | AB 7500 Fast Dx | | | Bio-Rad CFX96 Touch | | |
| −2 | 4,000,000 | 27 | 26 | 27 | 28 | 27 | 27 |
| −3 | 400,000 | 27 | 27 | 26 | 27 | 27 | 27 |
| −4 | 40,000 | 27 | 27 | 26 | 27 | 27 | 27 |
| −5 | 4,000 | 27 | 27 | 27 | 30 | 28 | 27 |
| −6 | 400 | 27 | 27 | 27 | 27 | 27 | 27 |
| HSC | 0 | 27 | 27 | 27 | 26 | 27 | 26 |

Manual Extraction Method Bridging Study
QIAGEN QIAamp® DSP Viral RNA Mini Kit—Limit of Detection Study A stock of Ebola virus prepared from a strain used in the original limit of detection study (Mayinga 1976) was quantified and inactivated by gamma irradiation. Four pools of serial 10-fold dilutions of this stock were prepared, then inactivated with TRIzol® LS (Life Technologies, catalog #10296-010) using a 5:1 dilution of TRIzol® to specimen. Each concentration was extracted five times using the QIAamp® DSP Viral RNA Mini Kit (QIAGEN, catalog #61904) to obtain an estimated LoD result. Resulting nucleic acid samples were tested by the EBOV VP40 rRT-PCR assay and the EBOV NP2 rRT-PCR assay. An additional 15 extractions at the estimated LoD concentration were performed to confirm the limit of detection. The confirmed limit of detection using the QIAamp® DSP Viral RNA Mini Kit was 6×10³ TCID$_{50}$/mL since 100% (20/20) results were positive at this concentration. Results of this LoD evaluation are presented in Table 28.

TABLE 28

VP40 and NP2 LoD Study Data

| TCID$_{50}$/ mL | NP2 positive results | | VP40 Positive Results | |
|---|---|---|---|---|
| | Range-finding | Verification | Range-finding | Verification |
| 6 × 10⁵ | 5/5 | | 5/5 | |
| 6 × 10⁴ | 5/5 | | 5/5 | |
| 6 × 10³ | 5/5 | 15/15 | 5/5 | 15/15 |
| 600 | 2/5 | | 3/5 | |
| HSC | 0/1 | 0/1 | 0/1 | 0/1 |
| NTC | 0/1 | 0/1 | 0/1 | 0/1 |

*RP generated similar results across pools as all pools were prepared with human whole blood.
HSC—Human Specimen Control,
NTC—No-Template Control Assay Performance Verification—Bo, Sierra Leone A study in Bo, Sierra Leone, was conducted to demonstrate the similarity of performance characteristics of the Ebola Virus VP40 Real-time RT-PCR Assay (EBOV VP40 rRT-PCR) and the Ebola Virus NP2 Real-time RT-PCR Assay (EBOV NP2 rRT-PCR) in the context of a field laboratory. The study evaluated the limit of detection, precision, and repeatability of the VP40 primer and probe set and the NP2 primer and probe set. The data generated in these performance verifications are presented below.

Limit of Detection—Field Laboratory Verification

Limit of detection for the EBOV VP40 rRT-PCR Assay primer and probe set and the EBOV NP2 rRT-PCR Assay primer and probe set was verified in the Bo field laboratory using the high concentration lyophilized spiked serum specimens from the Proficiency Testing (PT) Panel. This human serum specimen, spiked with inactivated (gamma irradiated) Ebola virus (Mayinga 1976) at 250,000 TCID$_{50}$/mL prior to lyophilization, was rehydrated per PT Panel package directions and used to prepare 10-fold serial dilutions in healthy human sera. Four dilutions were prepared, from 25,000 TCID$_{50}$/mL to 25 TCID$_{50}$/mL. Each dilution was extracted in triplicate using the MagMax Pathogen RNA/DNA Kit on the Dynal BeadRetriever System. Each resulting nucleic acid sample was then tested using the EBOV VP40 rRT-PCR assay and the EBOV NP2 rRT-PCR Assay on the CFX96 Touch to determine the range to be evaluated. Two concentrations, 250 TCID$_{50}$/mL and 2500 TCID$_{50}$/mL, were selected for further testing. These two concentrations were extracted an additional 20 times by the same extraction method. Each nucleic acid sample was tested by the EBOV VP40 rRT-PCR Assay and by the EBOV NP2 rRT-PCR Assay on the CFX96 Touch. All controls (HSC, NTC and Positive Control) generated expected results. The lowest concentration generating at least 95% positive results for VP40 or NP2 was considered the confirmed limit of detection for the EBOV VP40 rRT-PCR assay, or the EBOV NP2 rRT-PCR Assay, respectively.

TABLE 29

Limit of Detection Field Laboratory Verification - Confirmed Limit of Detection Summary

| Primer and Probe set | Extraction method | PCR instrument | Limit of Detection |
|---|---|---|---|
| VP40 | Dynal BeadRetriever | CFX96 Touch | 250 TCID$_{50}$/mL |
| NP2 | Dynal BeadRetriever | CFX96 Touch | 2500 TCID$_{50}$/mL |

The confirmed LoD from this field study is 250 TCID$_{50}$/mL for the EBOV VP40 rRT-PCR Assay primer and probe set, which is consistent with the LoD data generated with the same PCR instrument in conventional laboratories. Although the confirmed LoD from this field evaluation based on the at least 95% positivity criterion was 2500 TCID$_{50}$/mL for the EBOV VP40 rRT-PCR Assay primer and probe set, positivity of 91.3% (21/23) (95% CI: 73.2%-97.6%) was observed at 250 TCID$_{50}$/mL. Thus, the LoD from this field evaluation for the EBOV VP40 rRT-PCR Assay primer and probe set most likely falls between 250 TCID$_{50}$/mL and 2500 TCID$_{50}$/mL, which is consistent with the LoD data generated with the same PCR instrument in conventional laboratories.

Precision and Repeatability—Field Laboratory Verification

Precision of the EBOV VP40 rRT-PCR Assay and the EBOV NP2 rRT-PCR Assay was evaluated in the field laboratory in Bo, Sierra Leone using a Proficiency Testing (PT) Panel containing 6 lyophilized contrived serum specimens. Of the 6 specimens, two had been spiked with inactivated (gamma irradiated) Ebola virus (Mayinga 1976) at $2.5 \times 10^5$ TCID$_{50}$/mL prior to lyophilization, two had been spiked with this inactivated Ebola virus at $2.5 \times 10^3$ TCID$_{50}$/mL, and two contained no Ebola virus. Each day of testing, a fresh panel was rehydrated per PT panel package directions. Two operators each tested the PT panel members once a day for five days. Each panel member was extracted once using the MagMax Pathogen RNA/DNA Kit (Life Technologies, Cat #4462359) on the Dynal BeadRetriever™ System (Life Technologies, catalog #159-50). Each extracted RNA sample was then tested in triplicates on the CFX96 Touch Real-Time PCR instrument. A total of 30 data points for each concentration level tested per operator were generated for the precision study. Summaries of the qualitative results of this precision study are presented in Table 30.

TABLE 30

Qualitative summary (Percent agreement with expected result, each PCR replicate considered separately)

| Concentration | Operator 1 | | | Operator 2 | | |
|---|---|---|---|---|---|---|
| (Samples | VP40 | NP2 | RP | VP40 | NP2 | RP |
| Neat | 100% (30/30) | 100% (30/30) | 100% (30/30) | 100% (30/30) | 100% (30/30) | 100% (30/30) |
| 2500 TCID$_{50}$/mL | 100% (30/30) | 96.67% (29/30)* | 100% (30/30) | 100% (30/30) | 100% (30/30) | 100% (30/30) |
| 250,000 TCID$_{50}$/mL | 100% (30/30) | 100% (30/30) | 100% (30/30) | 100% (30/30) | 100% (30/30) | 100% (30/30) |

*One replicate on Day 1 failed to generate a positive result due to the presence of a deceased insect in the lid of the CFX96 Touch directly over well B1, obstructing the view of the optical unit.

Assessment of the qualitative results of the study demonstrates that the assay is repeatable in hands of multiple operators and at a site separate from the facility where the assay was developed. All but one result matched expected results for the NP2 assay, and all results matched expectations for the VP40 assay.

Additional analysis of the Ct values generated for the VP40 primer and probe set and the NP2 primer and probe set was conducted for each run, for each operator and overall. To evaluate precision of the assay, standard deviation (SD) was calculated for VP40 Ct values and NP2 Ct values at each concentration generated by Operator 1. This data was evaluated for each run, as well as for the entire data set generated by Operator 1. No standard deviation calculated for either concentration for any run or combination of runs ever exceeded 1, demonstrating the assays to be sufficiently precise in the hands of users in the field laboratory in Bo, Sierra Leone.

To evaluate the repeatability of the assay, data from both operators was evaluated based on coefficients of variance (CV). For both Ebola virus concentrations, the CV was calculated for each run, for each operator and for the overall data set. The CV never exceeded 3% for any run or combination of runs, demonstrating the assay to be repeatable. The overall coefficient of variance at the high concentration was 2.00%. The overall coefficient of variance at the low concentration was 1.60%. Summaries by run and by operator are presented in Table 31 below.

TABLE 31

Precision and repeatability data for VP40 Primer and Probe Set

| | | | | Run 1 | Run 2 | Run 3 | Run 4 | Run 5 | All Days |
|---|---|---|---|---|---|---|---|---|---|
| VP40 | 250,000 TCID$_{50}$/mL | Operator 1 | Replicates | 6 | 6 | 6 | 6 | 6 | 30 |
| | | | # Positive | 6 | 6 | 6 | 6 | 6 | 30 |
| | | | Average Ct | 26.15 | 27.06 | 27.05 | 27.15 | 27.11 | 26.90 |
| | | | SD | 0.103 | 0.097 | 0.121 | 0.137 | 0.160 | 0.400 |
| | | | % CV | 0.40% | 0.36% | 0.45% | 0.51% | 0.59% | 1.49% |
| | | Operator 2 | Replicates | 6 | 6 | 6 | 6 | 6 | 30 |
| | | | # Positive | 6 | 6 | 6 | 6 | 6 | 30 |
| | | | Average Ct | 27.30 | 26.50 | 27.95 | 26.46 | 26.34 | 26.91 |
| | | | SD | 0.141 | 0.162 | 0.282 | 0.233 | 0.127 | 0.655 |
| | | | % CV | 0.52% | 0.61% | 1.01% | 0.88% | 0.48% | 2.43% |
| | | All Operators | Replicates | | | | | | 60 |
| | | | # Positive | | | | | | 60 |
| | | | Average Ct | | | | | | 26.91 |
| | | | SD | | | | | | 0.538 |
| | | | % CV | | | | | | 2.00% |

TABLE 31-continued

Precision and repeatability data for VP40 Primer and Probe Set

| | | | | Run 1 | Run 2 | Run 3 | Run 4 | Run 5 | All Days |
|---|---|---|---|---|---|---|---|---|---|
| VP40 | 2500 TCID$_{50}$/mL | Operator 1 | Replicates | 6 | 6 | 6 | 6 | 6 | 30 |
| | | | # Positive | 5 | 6 | 6 | 6 | 6 | 30 |
| | | | Average Ct | 32.87 | 33.75 | 33.67 | 33.82 | 33.77 | 33.58 |
| | | | SD | 0.218 | 0.118 | 0.102 | 0.313 | 0.172 | 0.407 |
| | | | % CV | 0.66% | 0.35% | 0.30% | 0.92% | 0.51% | 1.21% |
| | | Operator 2 | Replicates | 6 | 6 | 6 | 6 | 6 | 30 |
| | | | # Positive | 6 | 6 | 6 | 6 | 6 | 30 |
| | | | Average Ct | 33.81 | 33.05 | 34.65 | 33.23 | 33.14 | 33.58 |
| | | | SD | 0.162 | 0.185 | 0.296 | 0.355 | 0.148 | 0.649 |
| | | | % CV | 0.48% | 0.56% | 0.85% | 1.07% | 0.45% | 1.93% |
| | | All Operators | Replicates | | | | | | 60 |
| | | | # Positive | | | | | | 60 |
| | | | Average Ct | | | | | | 33.58 |
| | | | SD | | | | | | 0.537 |
| | | | % CV | | | | | | 1.60% |

One run performed by Operator 2 was excluded from the analysis. A power interruption was encountered and curves generated during the run were abnormal. The run was repeated and the repeat data are presented in Table 31.

To evaluate the repeatability of the assay, data from both operators was evaluated based on coefficients of variance (CV). For both Ebola virus concentrations, the CV was calculated for each run, for each operator and for the overall data set. The CV never exceeded 3% for any run or combination of runs, demonstrating the assay to be repeatable. The overall coefficient of variance at the high concentration was 1.79%. The overall coefficient of variance at the low concentration was 1.76%. Summaries by run and by operator are presented in Table 32 below.

One run performed by Operator 2 was excluded from the analysis. A power interruption was encountered and curves generated during the run were abnormal. The run was repeated and the repeat data are presented in Table 32.

Example 2

Field Use of the EBOV VP40 rRT-PCR Assay and the EBOV NP2 rRT-PCR Assay to Screen Patient Samples for EBOV The EBOV VP40 rRT-PCR Assay and the EBOV NP2 rRT-PCR Assay were each used to test clinical samples for EBOV nucleic acid in a field laboratory in Bo, Sierra Leone.

TABLE 32

Precision and repeatability data for NP2 Primer and Probe Set

| | | | | Run 1 | Run 2 | Run 3 | Run 4 | Run 5 | All Days |
|---|---|---|---|---|---|---|---|---|---|
| NP2 | 250,000 TCID$_{50}$/mL | Operator 1 | Replicates | 6 | 6 | 6 | 6 | 6 | 30 |
| | | | # Positive | 6 | 6 | 6 | 6 | 6 | 30 |
| | | | Average Ct | 27.36 | 28.28 | 28.37 | 28.59 | 28.48 | 28.22 |
| | | | SD | 0.131 | 0.165 | 0.183 | 0.172 | 0.147 | 0.473 |
| | | | % CV | 0.48% | 0.59% | 0.64% | 0.60% | 0.52% | 1.68% |
| | | Operator 2 | Replicates | 6 | 6 | 6 | 6 | 6 | 30 |
| | | | # Positive | 6 | 6 | 6 | 6 | 6 | 30 |
| | | | Average Ct | 28.37 | 28.03 | 28.72 | 27.36 | 27.69 | 28.04 |
| | | | SD | 0.156 | 0.253 | 0.193 | 0.249 | 0.096 | 0.524 |
| | | | % CV | 0.55% | 0.90% | 0.67% | 0.91% | 0.34% | 1.87% |
| | | All Operators | Replicates | | | | | | 60 |
| | | | # Positive | | | | | | 60 |
| | | | Average Ct | | | | | | 28.13 |
| | | | SD | | | | | | 0.503 |
| | | | % CV | | | | | | 1.79% |
| NP2 | 2500 TCID$_{50}$/mL | Operator 1 | Replicates | 6 | 6 | 6 | 6 | 6 | 30 |
| | | | # Positive | 5 | 6 | 6 | 6 | 6 | 30 |
| | | | Average Ct | 33.83 | 34.73 | 35.01 | 35.32 | 34.96 | 34.80 |
| | | | SD | 0.068 | 0.161 | 0.305 | 0.184 | 0.136 | 0.521 |
| | | | % CV | 0.20% | 0.46% | 0.87% | 0.52% | 0.39% | 1.50% |
| | | Operator 2 | Replicates | 6 | 6 | 6 | 6 | 6 | 30 |
| | | | # Positive | 6 | 6 | 6 | 6 | 6 | 30 |
| | | | Average Ct | 35.34 | 35.23 | 35.78 | 34.79 | 34.42 | 35.11 |
| | | | SD | 0.219 | 0.338 | 0.447 | 0.938 | 0.060 | 0.666 |
| | | | % CV | 0.62% | 0.96% | 1.25% | 2.70% | 0.18% | 1.90% |
| | | All Operators | Replicates | | | | | | 60 |
| | | | # Positive | | | | | | 59 |
| | | | Average Ct | | | | | | 34.96 |
| | | | SD | | | | | | 0.614 |
| | | | % CV | | | | | | 1.76% |

Approximately 27,000 patient samples were tested using each assay. The samples included blood samples, oral swab samples and a few hundred semen samples. Each assay was reliable for all sample types tested, with negligible false-positive and false-negative rates.

It will be apparent that the precise details of the methods or compositions described may be varied or modified without departing from the spirit of the described embodiments. We claim all such modifications and variations that fall within the scope and spirit of the claims below.

We claim:

1. A method for detecting an EBOV NP nucleic acid in a biological sample from a subject, comprising:
   amplifying a DNA template produced from a reverse transcription reaction performed on nucleic acid containing RNA isolated from the biological sample by:
   contacting the DNA template under conditions suitable for amplification with a set of forward and reverse primers that can be used to amplify an EBOV nucleic acid molecule comprising the sequence set forth as SEQ ID NO: 1, and
   performing a polymerase chain reaction amplification to form an amplified DNA product; and
   contacting the amplified DNA product with a probe that can hybridize to the amplified DNA product;
   wherein hybridization of the probe to the amplified DNA product indicates that EBOV NP nucleic acid is present in the sample.

2. The method of claim 1, wherein the polymerase chain reaction amplification comprises a real-time polymerase chain reaction (RT-PCT).

3. The method of claim 1, wherein the set of primers comprises a forward primer comprising, consisting essentially of, or consisting of the nucleic acid sequence set forth as SEQ ID NO: 2 (NP2-F).

4. The method of claim 1, wherein the set of primers comprises a reverse primer comprising, consisting essentially of, or consisting of the nucleic acid sequence set forth as SEQ ID NO: 3 (NP2-R).

5. The method of claim 1, wherein the set of primers comprises a forward primer and a reverse primer comprising, consisting essentially of, or consisting of the nucleic acid sequences set forth as SEQ ID NO: 2 (NP2-F) and SEQ ID NO: 3 (NP2-R), respectively.

6. The method of claim 1, wherein the set of primers comprises a pair of reverse primers comprising, consisting essentially of, or consisting of the nucleic acid sequences set forth as SEQ ID NOs: 15 (NP2-R1) and 16 (NP2-R2).

7. The method of claim 1, wherein the set of primers comprises:
   a forward primer comprising, consisting essentially of, or consisting of the nucleic acid sequence set forth as SEQ ID NO: 2 (NP2-F), and a pair of reverse primers comprising, consisting essentially of, or consisting of the nucleic acid sequences set forth as SEQ ID NOs: 15 (NP2-R1) and 16 (NP2-R2).

8. The method of claim 1, wherein the probe comprises or consists of the nucleotide sequence set forth as SEQ ID NO: 4 (NP2-P), or the complement thereof.

9. The method of claim 1, wherein the set of primers comprises a forward primer comprising, consisting essentially of, or consisting of the nucleic acid sequence set forth as SEQ ID NO: 2 (NP2-F), and a pair of reverse primers comprising, consisting essentially of, or consisting of the nucleic acid sequences set forth as SEQ ID NOs: 15 (NP2-R1) and 16 (NP2-R2); and the probe comprises or consists of the nucleotide sequence set forth as SEQ ID NO: 4 (NP2-P), or the complement thereof.

10. The method of claim 1, wherein the set of primers comprises a forward primer consisting of the nucleic acid sequence set forth as SEQ ID NO: 2 (NP2-F), and a pair of reverse primers consisting of the nucleic acid sequences set forth as SEQ ID NOs: 15 (NP2-R1) and 16 (NP2-R2); and the probe consists of the nucleotide sequence set forth as SEQ ID NO: 4 (NP2-P), or the complement thereof.

11. A method for detecting an EBOV VP40 nucleic acid in a biological sample from a subject, comprising:
 amplifying a DNA template produced from a reverse transcription reaction performed on nucleic acid containing RNA isolated from the biological sample by:
  contacting the DNA template under conditions suitable for amplification with a set of forward and reverse primers that can be used to amplify an EBOV nucleic acid molecule comprising the sequence set forth as SEQ ID NO: 5, and
  performing a polymerase chain reaction amplification to form an amplified DNA product; and
 contacting the amplified DNA product with a probe that can hybridize to the amplified DNA product;
 wherein hybridization of the probe to the amplified DNA product indicates that EBOV NP nucleic acid is present in the sample.

12. The method of claim 1, further comprising detecting the amplified DNA product hybridized to the probe, wherein detecting hybridization of the probe to the amplified DNA product indicates that EBOV NP nucleic acid is present in the sample.

13. The method of claim 1, further comprising providing the DNA template.

14. The method of claim 1, wherein the probe is labeled with a detectable moiety that provides a detectable signal.

15. The method of claim 14, wherein the probe is labeled with a terminally-linked fluorophore and a terminally-linked non-fluorescent quencher for use in a RT-PCR assay.

16. The method of claim 1, wherein:
 detecting the amplified DNA product hybridized to the probe comprises determining a threshold cycle (Ct) of the test amplification; and
 determining if the probe is hybridized to the amplified DNA product comprises determining that the Ct of the test amplification is less than the Ct of a negative control RT-PCR amplification performed using the forward and reverse primers and the probe on a sample lacking EBOV nucleic acid.

17. The method of claim 16, wherein the threshold cycle of the test amplification is 38 cycles or fewer.

18. The method of claim 1, wherein the DNA template is produced by:
 isolating the nucleic acid containing RNA from the biological sample; and
 performing the reverse transcription reaction on the isolated nucleic acid to produce the DNA template.

19. The method of claim 1, wherein the biological sample is a blood, serum, plasma, or urine sample.

20. The method of claim 1, wherein the subject has or is at risk of an EBOV infection.

21. The method of claim 1, wherein the method detects EBOV nucleic acid from at least 95% of EBOV isolates.

22. The method of claim 1, further comprising identifying the subject as a subject with an EBOV infection if EBOV nucleic acid is detected in the biological sample.

23. The method of claim 22, further comprising treating EBOV infection in the subject.

24. The method of claim 23, comprising administering a therapeutically effective amount of an anti-Ebola agent to the subject.

* * * * *

SEQUENCE LISTING

```
<160> NUMBER OF SEQ ID NOS: 16

<210> SEQ ID NO 1
<211> LENGTH: 119
<212> TYPE: DNA
<213> ORGANISM: Ebola virus

<400> SEQUENCE: 1
attgctgcca gcagtatcta gtgggagaaa cattaagaga acacttgctg ccatgccgga      60
agaggagacg actgaagcta atgccggtca gttcctctcc tttgcaagtc tattccttc     119

<210> SEQ ID NO 2
<211> LENGTH: 25
<212> TYPE: DNA
<213> ORGANISM: artificial sequence
<220> FEATURE:
<223> OTHER INFORMATION: oligonucleotide

<400> SEQUENCE: 2
aattgctgcc agcagtatct agtgg                                            25

<210> SEQ ID NO 3
<211> LENGTH: 25
<212> TYPE: DNA
<213> ORGANISM: artificial sequence
<220> FEATURE:
<223> OTHER INFORMATION: oligonucleotide

<400> SEQUENCE: 3
gaaggaatag acttgcaaar gagag                                            25

<210> SEQ ID NO 4
<211> LENGTH: 32
<212> TYPE: DNA
<213> ORGANISM: artificial sequence
<220> FEATURE:
<223> OTHER INFORMATION: oligonucleotide

<400> SEQUENCE: 4
tctcctcttc cggcatggca gcaagtgttc tc                                    32

<210> SEQ ID NO 5
<211> LENGTH: 67
<212> TYPE: DNA
<213> ORGANISM: Ebola virus

<400> SEQUENCE: 5
tgcgtccagg aatttcattt catccaaaac ttcgccccat tcttttaccc aacaaaagtg      60
ggaagaa                                                                67

<210> SEQ ID NO 6
<211> LENGTH: 17
<212> TYPE: DNA
<213> ORGANISM: artificial sequence
<220> FEATURE:
<223> OTHER INFORMATION: oligonucleotide

<400> SEQUENCE: 6
```
tgcgyccagg aatttca                                                  17

<210> SEQ ID NO 7
<211> LENGTH: 23
<212> TYPE: DNA
<213> ORGANISM: artificial sequence
<220> FEATURE:
<223> OTHER INFORMATION: oligonucleotide

<400> SEQUENCE: 7
ttcttcccac tyttgttggg taa                                           23

<210> SEQ ID NO 8
<211> LENGTH: 24
<212> TYPE: DNA
<213> ORGANISM: artificial sequence
<220> FEATURE:
<223> OTHER INFORMATION: oligonucleotide

<400> SEQUENCE: 8
tcatccaaaa ctkcgcccca ttct                                          24

<210> SEQ ID NO 9
<211> LENGTH: 17
<212> TYPE: DNA
<213> ORGANISM: artificial sequence
<220> FEATURE:
<223> OTHER INFORMATION: oligonucleotide

<400> SEQUENCE: 9
tgcgcccagg aatttca                                                  17

<210> SEQ ID NO 10
<211> LENGTH: 17
<212> TYPE: DNA
<213> ORGANISM: artificial sequence
<220> FEATURE:
<223> OTHER INFORMATION: oligonucleotide

<400> SEQUENCE: 10
tgcgtccagg aatttca                                                  17

<210> SEQ ID NO 11
<211> LENGTH: 23
<212> TYPE: DNA
<213> ORGANISM: artificial sequence
<220> FEATURE:
<223> OTHER INFORMATION: oligonucleotide

<400> SEQUENCE: 11
ttcttcccac tcttgttggg taa                                           23

<210> SEQ ID NO 12
<211> LENGTH: 23
<212> TYPE: DNA
<213> ORGANISM: artificial sequence
<220> FEATURE:
<223> OTHER INFORMATION: oligonucleotide

<400> SEQUENCE: 12
ttcttcccac ttttgttggg taa                                           23

<210> SEQ ID NO 13
<211> LENGTH: 24
<212> TYPE: DNA
<213> ORGANISM: artificial sequence

```
<220> FEATURE:
<223> OTHER INFORMATION: oligonucleotide

<400> SEQUENCE: 13
tcatccaaaa ctgcgcccca ttct                                              24

<210> SEQ ID NO 14
<211> LENGTH: 24
<212> TYPE: DNA
<213> ORGANISM: artificial sequence
<220> FEATURE:
<223> OTHER INFORMATION: oligonucleotide

<400> SEQUENCE: 14
tcatccaaaa cttcgcccca ttct                                              24

<210> SEQ ID NO 15
<211> LENGTH: 25
<212> TYPE: DNA
<213> ORGANISM: artificial sequence
<220> FEATURE:
<223> OTHER INFORMATION: oligonucleotide

<400> SEQUENCE: 15
gaaggaatag acttgcaaaa gagag                                             25

<210> SEQ ID NO 16
<211> LENGTH: 25
<212> TYPE: DNA
<213> ORGANISM: artificial sequence
<220> FEATURE:
<223> OTHER INFORMATION: oligonucleotide

<400> SEQUENCE: 16
gaaggaatag acttgcaaag gagag                                             25
```